(12) United States Patent
Shapiro et al.

(10) Patent No.: US 9,783,616 B2
(45) Date of Patent: Oct. 10, 2017

(54) REGULATING TRANSPLANT REJECTION OF DONOR AND EMBRYONIC STEM CELL-DERIVED TISSUES AND ORGANS

(71) Applicant: University of Connecticut, Farmington, CT (US)

(72) Inventors: Linda H. Shapiro, Farmington, CT (US); Jiyeon K. Denninger, Farmington, CT (US)

(73) Assignee: University of Connecticut, Farmington, CT (US)

( * ) Notice: Subject to any disclaimer, the term of this patent is extended or adjusted under 35 U.S.C. 154(b) by 18 days.

(21) Appl. No.: 14/779,629

(22) PCT Filed: Apr. 2, 2014

(86) PCT No.: PCT/US2014/032641
§ 371 (c)(1),
(2) Date: Sep. 24, 2015

(87) PCT Pub. No.: WO2014/165573
PCT Pub. Date: Oct. 9, 2014

(65) Prior Publication Data
US 2016/0053021 A1 Feb. 25, 2016

Related U.S. Application Data

(60) Provisional application No. 61/807,632, filed on Apr. 2, 2013.

(51) Int. Cl.
| | |
|---|---|
| *A61K 39/00* | (2006.01) |
| *A61K 48/00* | (2006.01) |
| *A61K 35/36* | (2015.01) |
| *A61K 35/39* | (2015.01) |
| *A61K 35/12* | (2015.01) |
| *C07K 16/40* | (2006.01) |
| *C12N 5/0735* | (2010.01) |
| *A61K 35/48* | (2015.01) |
| *A61K 35/00* | (2006.01) |

(52) U.S. Cl.
CPC .............. *C07K 16/40* (2013.01); *A61K 35/36* (2013.01); *A61K 35/48* (2013.01); *C12N 5/0606* (2013.01); *A61K 35/00* (2013.01); *A61K 2039/505* (2013.01); *C07K 2317/76* (2013.01); *C12N 2510/00* (2013.01)

(58) Field of Classification Search
CPC ...... A61K 35/36; A61K 35/545; A61K 35/12; A61K 35/28; A61K 2035/124; A61K 2039/505; A61K 39/395; A61K 2039/51
See application file for complete search history.

(56) References Cited

U.S. PATENT DOCUMENTS

2006/0211602 A1* 9/2006 Ansorge ................. A61K 31/66
514/1.9
2012/0230966 A1* 9/2012 Crawford ............... A61K 47/38
424/93.71

FOREIGN PATENT DOCUMENTS

WO 01/54707 A2 8/2001

OTHER PUBLICATIONS

Chan et al., "Live cell imaging distinguishes bona fide human iPS cells from partially reprogrammed cells", Nature Biotechnology, 2009, 27(11), 1033-1037.
Winnicka et al., "CD13 is dispensable for normal hematopoiesis and myeloid cell functions in the mouse", Journal of Leukocyte Biology, 2010, 88(2), 347-359.
Bauvois et al., "Aminopeptidase-N/CD13 (EC 3.4.11.2) inhibitors: chemistry, biological evaluations, and therapeutic prospects", Medicinal Research Reviews, 2006, 26(1), 88-130.
Osorio et al., "The moonlighting enzyme CD13: old and new functions to target", Trends in Molecular Medicine, 2008, 14(8), 361-371.
Ino et al., "Monocyte activation by an oral Immunomodulator (bestatin) in lymphoma patients following autologous bone marrow transplantation", Cancer Immunology and Immunotherapy, 1996, 43(4), 206-212.
Lis et al., "Modulatory effects of bestatin on T and B lymphocyte subsets and the concentration of cytokines released by Th1/Th2 lymphocytes in cyclophosphamide-treated mice", Central European Journal of Immunology, 2013, vol. 1, 42-53.
Rahman et al., "CD13 promotes mesenchymal stem cell-mediated regeneration of ischemic muscle", Frontiers in Physiology, 2014, vol. 4, 1-12.

* cited by examiner

*Primary Examiner* — Daniel C Gamett
(74) *Attorney, Agent, or Firm* — McDonnell Boehnen Hulbert & Berghoff LLP

(57) ABSTRACT

The invention provides methods and cells for improved transplantation of donor transplants to subjects in need thereof.

9 Claims, 17 Drawing Sheets

Figure 1
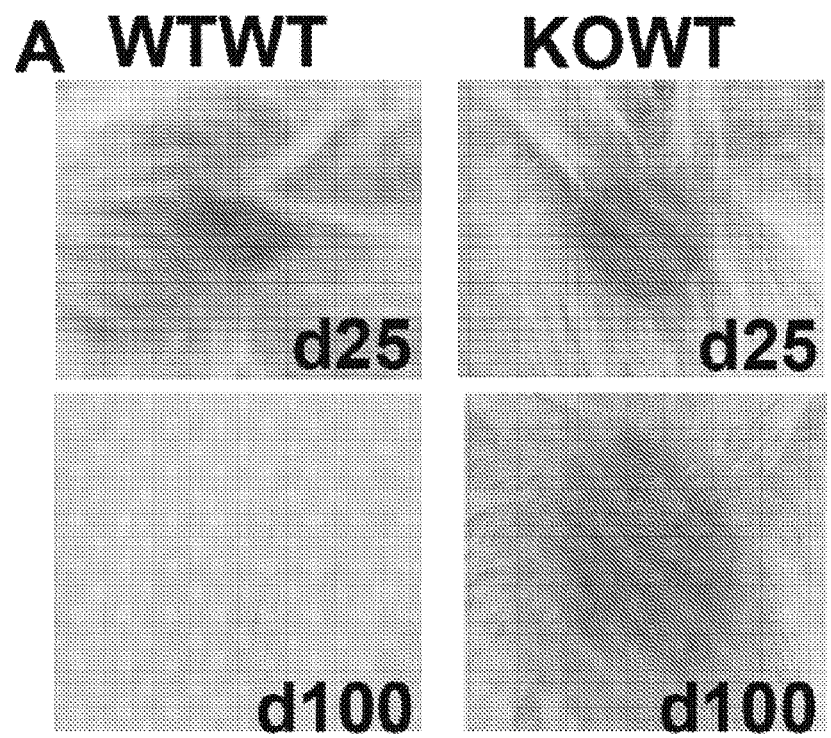
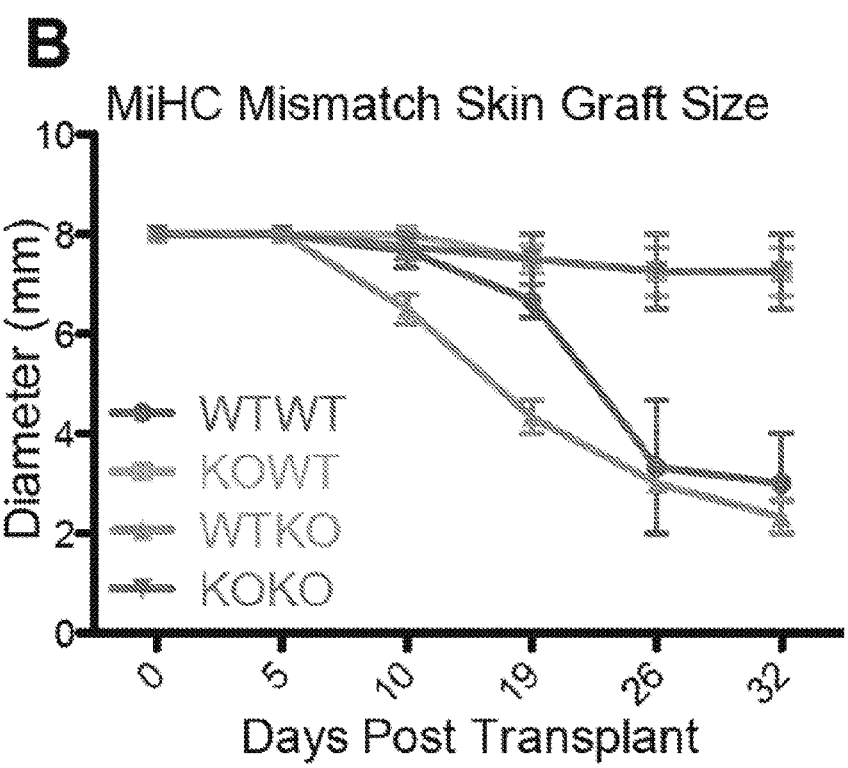

Figure 1
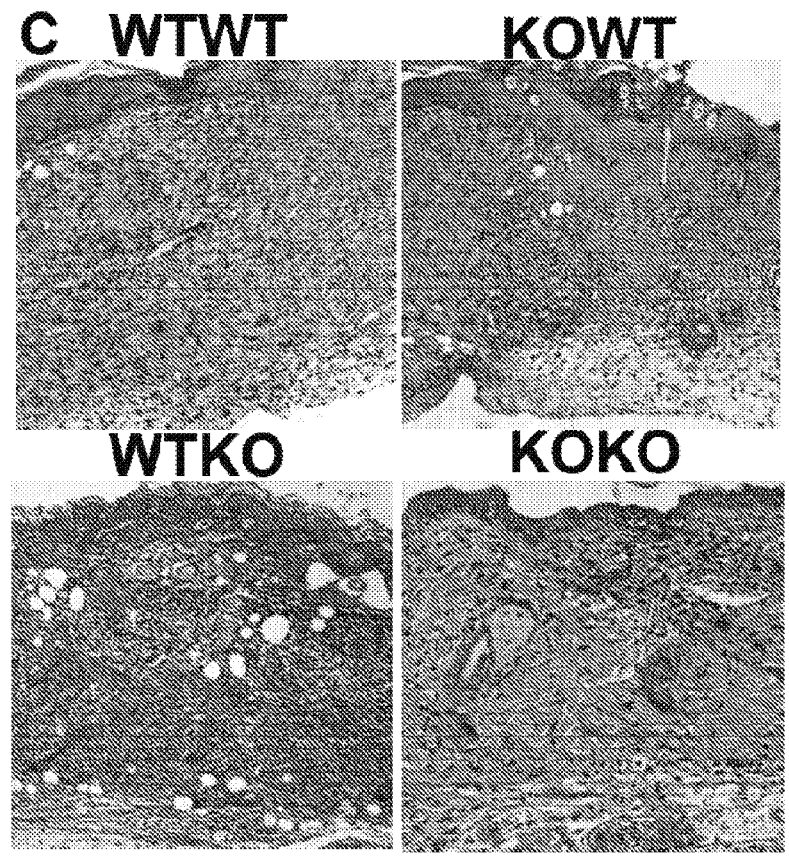
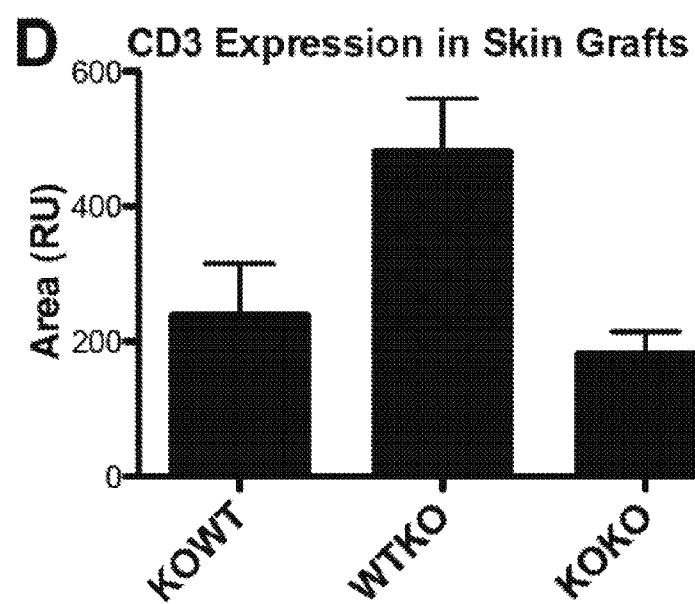

Figure 2
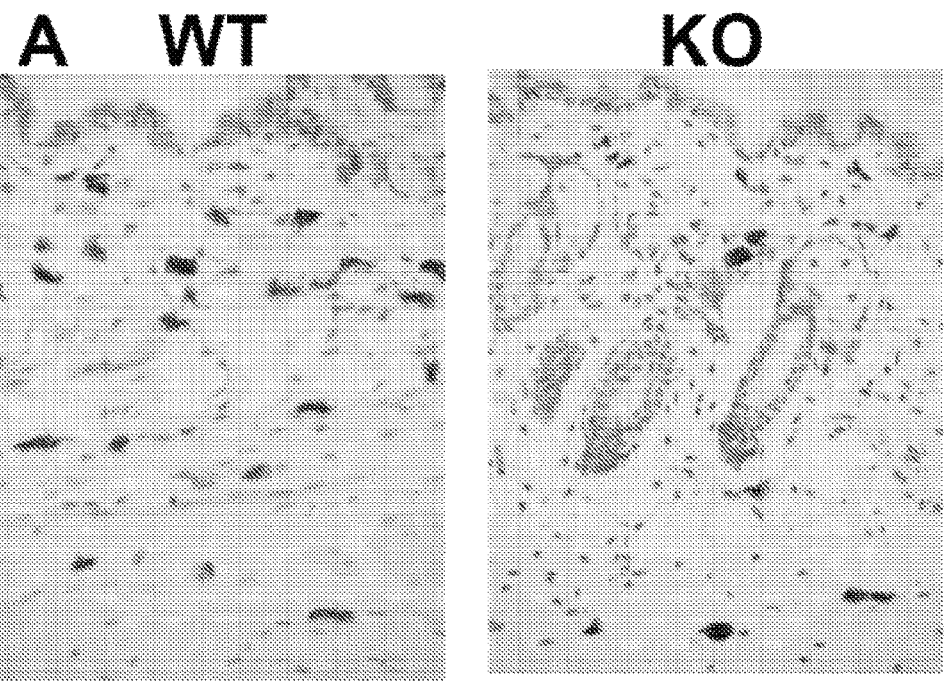
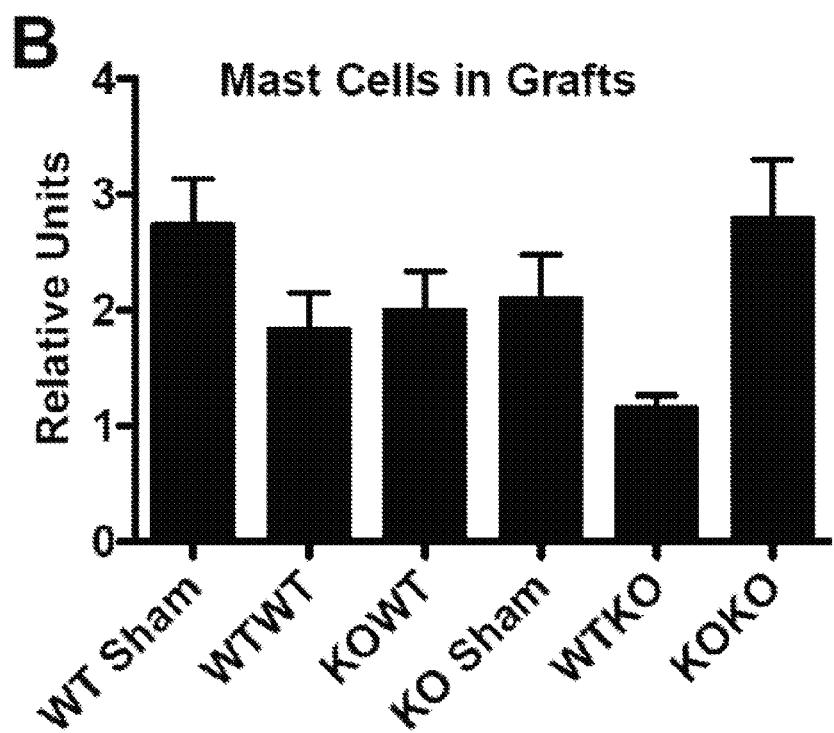

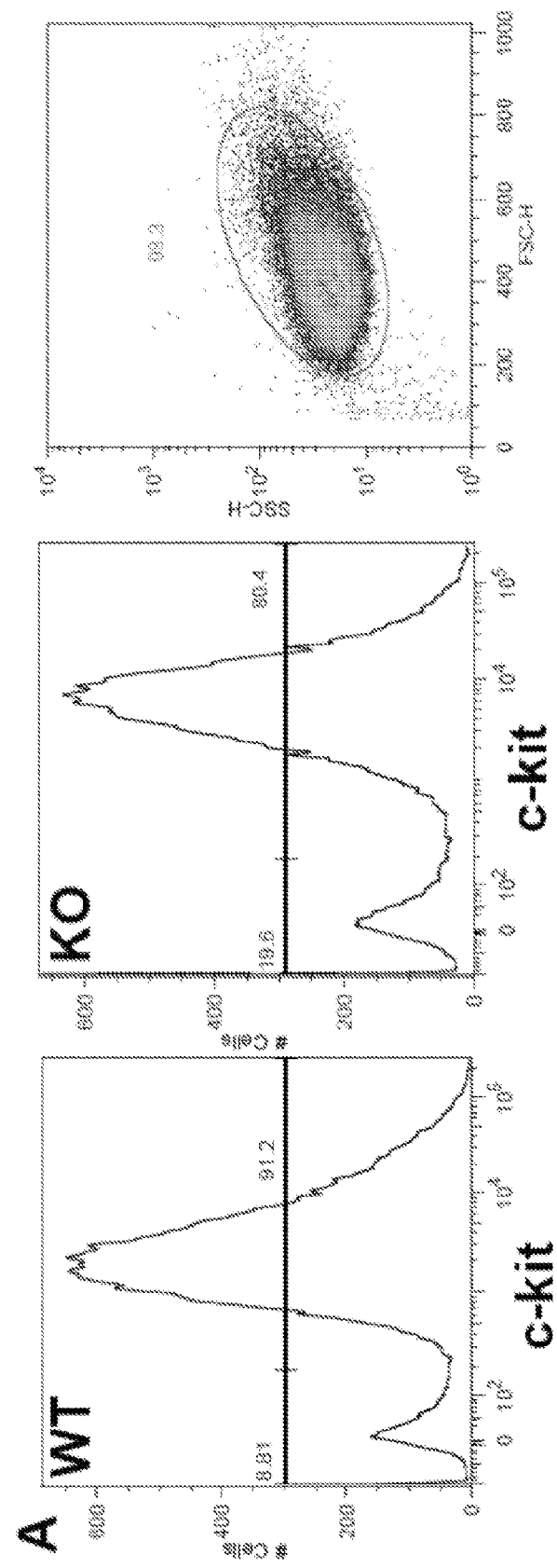

Figure 5
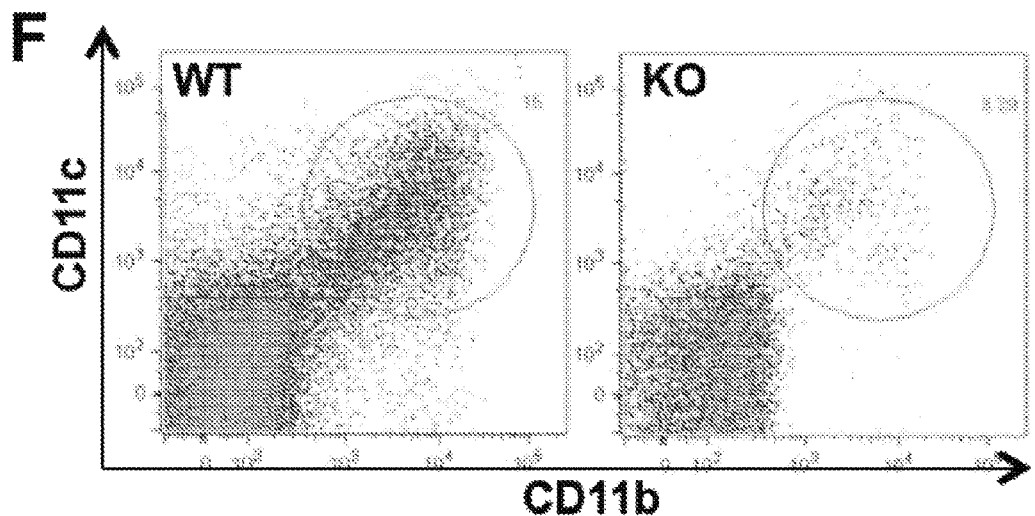
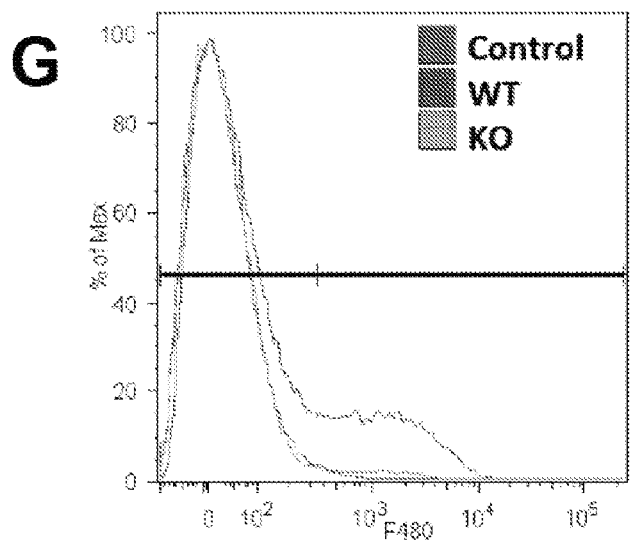
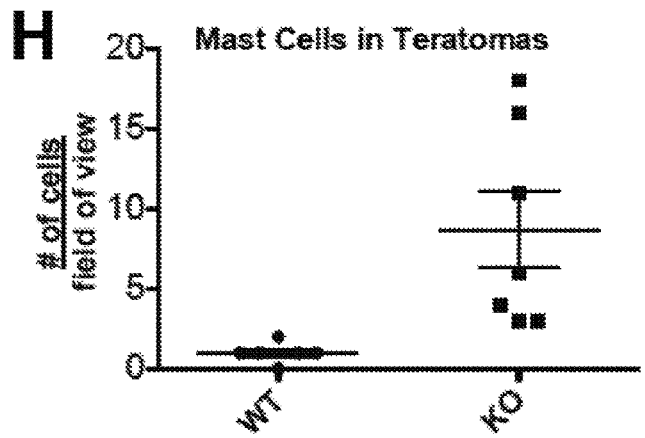

Figure 6
Murine Skin Graft Model
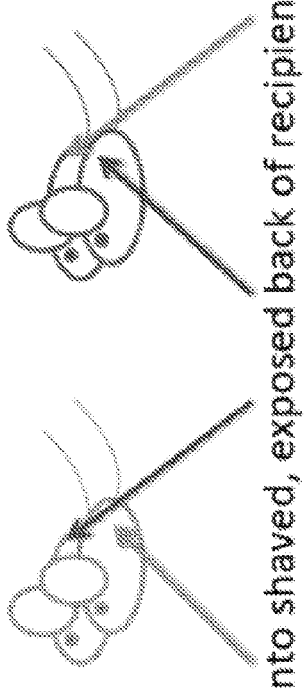
CD13 WT and KO Male Donor
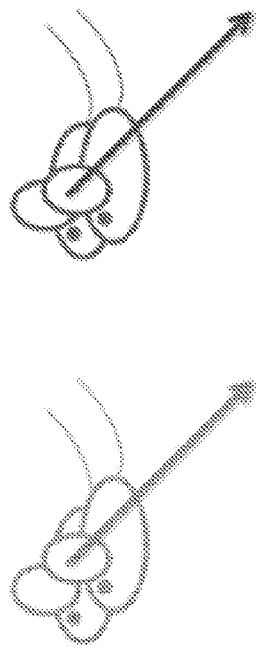
CD13 WT and KO Female Recipient
Harvest skin from dorsal side of ear and graft onto shaved, exposed back of recipients Figure 10
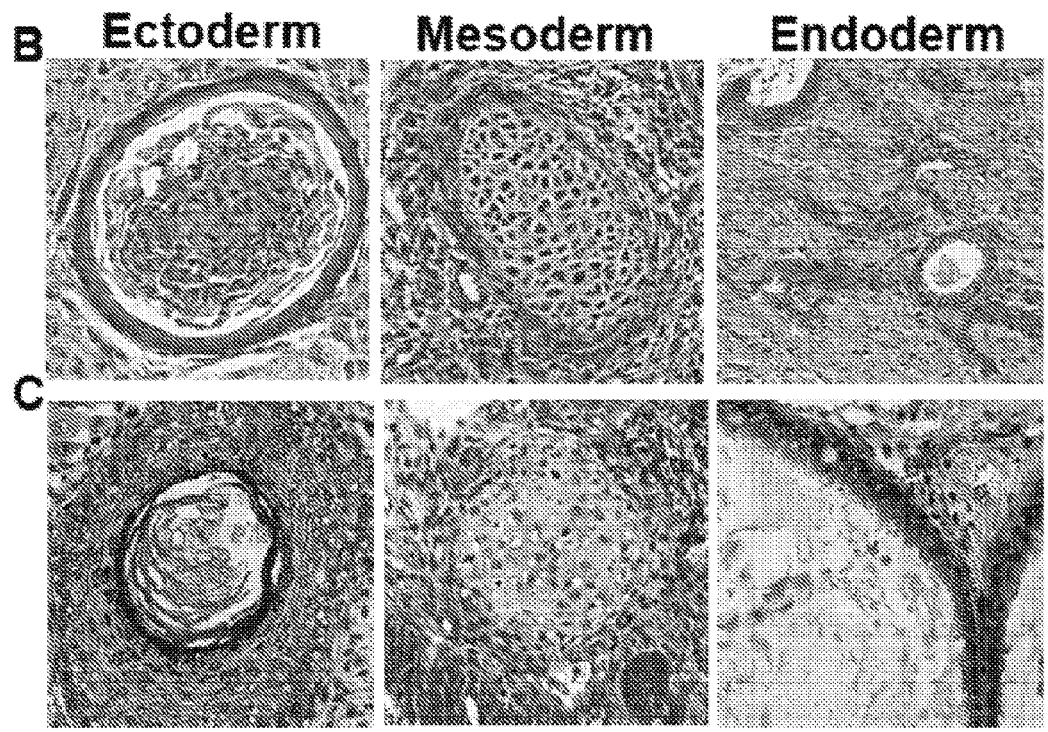
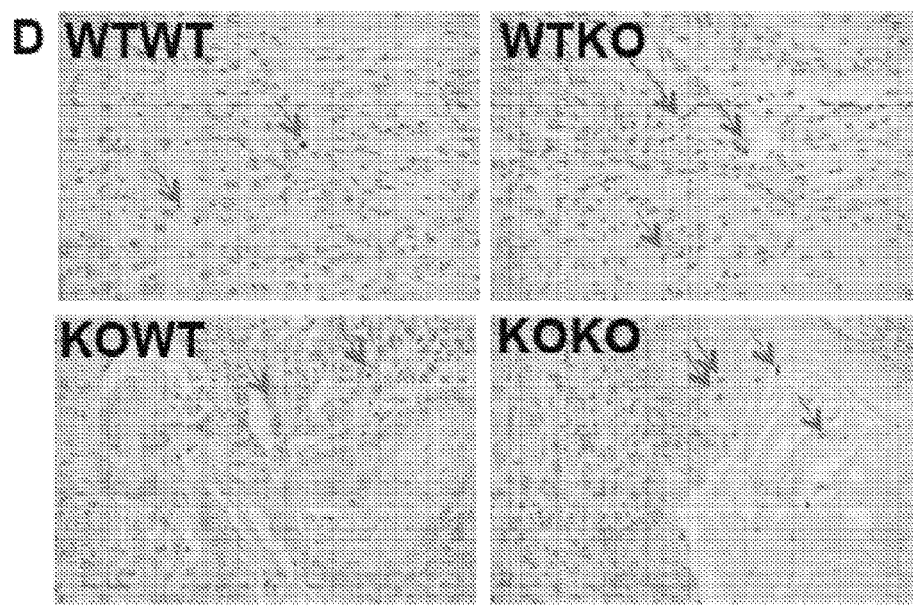

REGULATING TRANSPLANT REJECTION OF DONOR AND EMBRYONIC STEM CELL-DERIVED TISSUES AND ORGANS

CROSS-REFERENCE TO RELATED APPLICATIONS

This application is a U.S. national phase of International Application No. PCT/US2014/032641, filed Apr. 2, 2014, which claims the benefit of U.S. Provisional Application No. 61/807,632, filed Apr. 2, 2013, the disclosures of which are explicitly incorporated by reference herein in their entirety.

BACKGROUND

Stem cell therapy is a rapidly advancing field where huge strides have been made in the repair of critical organs. Unfortunately, as with any other graft, stem cell transplants have a high probability of developing immune-mediated complications ultimately resulting in rejection. While strategies such as host immune suppression or use of host-derived cells address the issue of rejection, they are not ideal due to compromised patient health or the prohibitive cost of individualized treatment. Identification of key triggers and development of novel, broadly applicable strategies to specifically control the immune response is imperative for wide scale implementation of cell therapies. Alanyl (membrane) aminopeptidase (ANPEP) is a cell surface protease expressed by monocytes, macrophages, dendritic cells, among many others. The inventors have recently identified ANPEP as a regulator of receptor-mediated antigen uptake and presentation in dendritic cells, an inflammatory adhesion molecule, a regulator of innate immunity, and a regulator of endocytosis, and tested whether ANPEP was involved in immune responses elicited by stem cell transplantation.

SUMMARY OF THE INVENTION

In a first aspect the invention provides a method of limiting development of transplant rejection, comprising administering to a subject in need thereof and/or treating a donor transplant with an effective amount of an inhibitor of alanyl (membrane) aminopeptidase (ANPEP) to treat or limit development of transplant rejection. The inhibitor can prevent the expression, activity and/or function of ANPEP; any suitable ANPEP inhibitor can be used, as deemed most appropriate for an intended use. In exemplary embodiments, the inhibitor can be selected from the group consisting of anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides and small molecule ANPEP inhibitors. In a preferred embodiment, the inhibitor is an anti-ANPEP antibody (i.e., an antibody that binds to ANPEP).

In a second aspect the invention provides a pluripotent cell population, wherein the population does not express functional ANPEP. Functional ANPEP can be knocked out or inhibited by a method selected from generation of knock-in null mutant ANPEP cell population using homologous recombination, transcription activator-like effector nucleases (TALENs), clustered regulatory interspaced short palindromic repeat (CRISPR) Cas-based RNA-guided DNA endonucleases technology, generation of ANPEP knockout cell line using homologous recombination, TALEN or CRISPR technology, generation of knock-in point mutation of ANPEP using homologous recombination, TALEN or CRISPR technology, anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides and small molecule ANPEP inhibitors. In some embodiments, cells, tissues or organs derived from the pluripotent cell population that does not express functional ANPEP can be transplanted into a subject in need thereof.

BRIEF DESCRIPTION OF THE DRAWINGS

The disclosed exemplary aspects have other advantages and features which will be more readily apparent from the detailed description, the appended claims, and the accompanying figures. A brief description of the figures is below.

FIG. 1 shows that CD13-null skin grafts survive longer. (A) Gross images of wild type (WT) and CD13-null skin grafts in WT recipients at days 25 (top) and 100 (bottom). (B) Skin graft measurements over time demonstrate decreased diameter until complete rejection in WT grafts compared to CD13-null grafts. (C) H&E staining of skin graft sections demonstrate higher numbers of infiltrating cells WT compared to CD13-null skin grafts. (D) Quantification of immunohistochemical staining of skin graft sections demonstrate higher levels of CD3 staining, indicative of T cell infiltration, in WT grafts. WTWT=WT donor tissue. WT recipient; KOWT=KO donor tissue, WT recipient; WTKO=WT donor tissue. KO recipient; KOKO=KO donor tissue, KO recipient.

FIG. 6 shows a schematic for MiHC mismatch skin graft. Donor male skin is harvested from the dorsal side of the ear and transplanted onto the shaved exposed backs of female recipient mice.

DETAILED DESCRIPTION OF THE INVENTION

Figure 2:
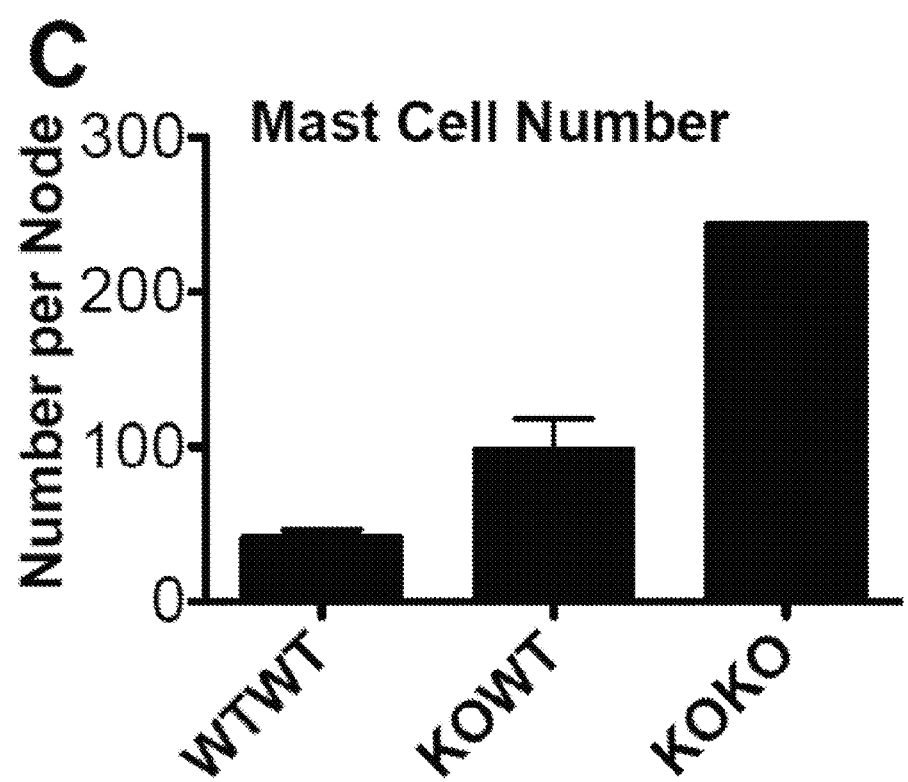
FIG. 2 shows that mast cell presence is higher in surviving grafts. (A) Toluidine blue staining of mast cell granules in skin at baseline. (B) Quantification of toluidine blue staining in skin graft tissue at days 5-7 post-transplant indicates loss of mast cell granule staining in WT graft tissue. (C) Quantification of toluidine blue staining in draining lymph nodes of mice receiving minor histocompatibility (MiHC) mismatch skin grafts demonstrates higher levels of mast cells that have not degranulated in recipients receiving CD13-null donor tissue.

Methods well known to those skilled in the art can be used to construct expression vectors and recombinant bacterial cells according to this invention. These methods include in vitro recombinant DNA techniques, synthetic techniques, in vivo recombination techniques, and PCR techniques. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York, and *PCR Protocols: A Guide to Methods and Applications* (Innis et al., 1990, Academic Press, San Diego, Calif.).

All publications, patents and patent applications cited herein are hereby expressly incorporated by reference for all purposes.

Before describing the present invention in detail, a number of terms will be defined. As used herein, the singular forms "a", "an", and "the" include plural referents unless the context clearly dictates otherwise. For example, reference to a "nucleic acid" means one or more nucleic acids.

In a first aspect the invention provides a method of limiting development of transplant rejection, comprising administering to a subject in need of a transplant and/or treating a donor transplant with an effective amount of an inhibitor of alanyl (membrane) aminopeptidase (ANPEP) to limit development of transplant rejection in the subject.

The inventors have surprisingly discovered that the methods of the invention allow the ability of donor transplant to engraft and survive with little to no immune suppression required of the recipient. Furthermore, the cells, tissues and organs of the invention in which ANPEP is inhibited or that do not express functional ANPEP can be transplanted universally without minor histocompatibility complex (MiHC) matching, human leukocyte antigen (HLA) matching or immune suppression. Thus, the inhibition of ANPEP expression, activity or function in a donor transplant or cells, tissues or organs to be transplanted can allow more successful transplantation by mitigating or eliminating the immune reactions triggered by transplantation.

For uses in this application, CD13 and ANPEP will be used synonymously. The approved HUGO Gene Nomenclature Committee (HGNC) Symbol for human CD13 is ANPEP, and the approved HGNC name is alanyl (membrane) aminopeptidase. Previous names include: CD13, PEPN; APN; LAP1; P150; GP150. Synonyms include: aminopeptidase M, aminopeptidase N, microsomal aminopeptidase. Human ANPEP has the following identifiers: UniProtKB/Swiss-Prot, P15144 (SEQ ID NO: 01); NCBI Reference Sequence (mRNA), NM_001150.2 (SEQ ID NO: 02); and NCBI Reference Sequence (protein), NP_001141.2 (SEQ ID NO: 03) and point mutations (SEQ ID NOs: 04-06). CD13 is a type II zinc-dependent metallopeptidase that is found on the surface of all myeloid cells in addition to pericytes, activated endothelial cells, and subsets of organ-specific epithelial cells. It is a multifunctional protein with both enzyme-dependent and independent functions that contribute to adhesion, cell migration, angiogenesis, inflammatory trafficking, adhesion, antigen presentation, and endocytosis.

TABLE 1

ANPEP Sequences

Human Aminopeptidase N (EC = 3.4.11.2) ANPEP
>sp|P15144|AMPN_HUMAN Aminopeptidase N (SEQ ID NO: 01)
MAKGFYISKSLGILGILLGVAAVCTIIALSVVYSQEKNKNANSSPVASTTPSASATTNPASATTL
DQSKAWNRYRLPNTLKPDSYRVTLRPYLTPNDRGLYVFKGSSTVRFTCKEATDVIIHSKKLNYT
LSQGHRVVLRGVGGSQPPDIDKTELVEPTEYLVVHLKGSLVKDSQYEMDSEFEGELADDLAGFYR
SEYMEGNVRKVVATTQMQAADARKSFPCFDEPAMKAEFNITLIHPKDLTALSNMLPKGPSTPLPE
DPNWNVTEFHTTPKMSTYLLAFIVSEEDYVEKQASNGVLIRIWARPSAIAAGHGDYALNVTGPIL
NFFAGHYDTPYPLPKSDQIGLPDFNAGAMENWGLVTYRENSLLFDPLSSSSSNKERVVTVIAHEL
ASQWFGNLVTIEWWNDLWLNEGFASYVEYLGADYAEPTWNLKDLMVLNDVYRVMAVDALASSHPL
STPASEINTPAQISELFDAISYSKGASVLRMLSSFLSEDVFKQGLASYLHTFAYQNTIYLNLWDH
LQEAVNNRSIQLPTTVRDIMNRWTLQMGFPVITVDTSTGTLSQEHFLLDPDSNVTRPSEFNYVWI
VPITSIRDGRQQQDYWLIDVRAQNDLFSTSGNEWVLLNLNVTGYYRVNYDEENWRKIQTQLQRDH
SAIPVINRAQIINDAFNLASAHKVPVTLALNNTLFLIEERQYMPWEAALSSLSYFKLMPDRSEVY
GPMKNYLKKQVTPLFIHFRNNTNNWRIEPENLMDQYSEVNAISTACSNGVPECEEMVSGLFKQWM
ENPNNNPIHPNLRSTVYCNAIAQGGEEEWDFAWEQFRNATLVNEADKLRAALACSKELWILNRYL
SYTLNPDLIRKQDATSTIISITNNVIGQGLVWDFVQSNWKKLFNDYGGGSFSFSNLIQAVTRRFS
TEYELQQLEQFKKDNEETGFGSGTRALEQALEKTKANIKWVKENKEVVLQWFTENSK TABLE 1-continued ANPEP Sequences

*Homo sapiens* alanyl (membrane) aminopeptidase (ANPEP), mRNA NCBI Reference Sequence: NM_001150.2

(SEQ ID NO: 02)

```
gggacggcgg cggcgcagct cggaacccgc cagggtccag ggtccaggtt ccagcgcccg
gcggcccagg caccccccga gcccagctcc acacaccgtt cctggatctc ctctcccag
gcggagcgtg cccctgccca gtccagtgac cttcgcctgt tggagccctg gttaattttt
gcccagtctg cctgttgtgg ggctcctccc cttttgggat ataagcccgg cctggggctg
ctccgttctc tgcctggcct gaggctccct gagccgcctc cccaccatca ccatggccaa
gggcttctat atttccaagt ccctgggcat cctggggatc ctcctgggcg tggcagccgt
gtgcacaatc atcgcactgt cagtggtgta ctcccaggag aagaacaaga acgccaacag
ctccccggtg gcctccacca ccccgtccgc ctcagccacc accaaccccg cctcggccac
caccttggac caaagtaaag cgtggaatcg ttaccgcctc cccaacacgc tgaaacccga
ttcctaccgg gtgacgctga ccgtacct caccccaat gacagggggcc tgtacgtttt
taagggctcc agcaccgtcc gtttcacctg caaggaggcc actgacgtca tcatcatcca
cagcaagaag ctcaactaca ccctcagcca ggggcacagg gtggtcctgc gtggtgtggg
aggctcccag ccccccgaca ttgacaagac tgagctggtg gagcccaccg agtacctggt
ggtgcacctc aagggctccc tggtgaagga cagccagtat gagatggaca gcagttcga
gggggagttg gcagatgacc tggcgggctt ctaccgcagc gagtacatgg agggcaatgt
cagaaaggtg gtggccacta cacagatgca ggctgcagat gcccggaagt ccttccccat
cttcgatgag ccggccatga aggccgagtt caacatcacg cttatccacc caaggacct
gacagccctg tccaacatgc ttcccaaagg tcccagcacc ccacttccag aagaccccaa
ctggaatgtc actgagttcc acaccacgcc caagatgtcc acgtacttgc tggccttcat
tgtcagtgag ttcgactacg tggagaagca ggcatccaat ggtgtcttga tccggatctg
ggcccggccc agtgccattg cggcgggcca cggcgattat gccctgaacg tgacgggccc
catccttaac ttctttgctg gtcattatga cacaccctac ccactcccaa aatcagacca
gattggcctg ccagacttca cgccggcgc catggagaac tggggactgg tgacctaccg
ggagaactcc ctgctgttcg accccctgtc ctcctccage agcaacaagg agcgggtggt
cactgtgatt gctcatgagc tggcccacca gtggttcggg aacctggtga ccatagagtg
gtggaatgac ctgtggctga cgagggcttg cgcctcctac gtgagtacc tgggtgctga
ctatgcggag cccacctgga acttgaaaga cctcatggtg ctgaatgatg tgtaccgcgt
gatggcagtg gatgcactgg cctcctccca cccgctgtcc acacccgcct cggagatcaa
cacgccggcc cagatcagtg agctgtttga cgccatctcc tacagcaagg gcgcctcagt
cctcaggatg ctctccagct tcctgtccga ggacgtattc aagcagggcc tggcgtccta
cctccacacc tttgcctacc agaacaccat ctacctgaac ctgtgggacc acctgcagga
ggctgtgaac aaccggtcca tccaactccc caccaccgtg cgggacatca tgaaccgctg
gacctgcagg atgggcttcc cggtcatcac ggtggataac agcacgggga ccctttccca
ggagcacttc ctccttgacc ccgattccaa tgttacccgc ccctcagaat tcaactacgt
gtggattgtg cccatcacat ccatcagaga tggcagacag cagcaggact actggctgat
agatgtaaga gcccagaacg atctcttcag cacatcaggc aatgagtggg tcctgctgaa
cctcaatgtg acgggctatt accgggtgaa ctacgacgaa gagaactgga gaagattca
gactcagctg cagagagacc actcggccat ccctgtcatc aatcgggcac agatcattaa
tgacgccttc aacctggcca gtgcccataa ggtccctgtc actctggcgc tgaacaacac
cctcttcctg attgaagaga gacagtacat gcccctggga gccgccctga gcagcctgag
ctacttcaag ctcatgtttg accgctccga ggtctatggc cccatgaaga actacctgaa
gaagcaggtc acacccctct tcattcactt cagaaataat accaacaact ggagggagat
cccagaaac ctgatggacc agtacagcga ggttaatgcc atcagcaccg cctgctccaa
cggagttcca gagtgtgagg agatggtctc tggcctttc aagcagtgga tggagaaccc
caataataac ccgatccacc ccaacctgcg gtccaccgtc tactgcaacg ctatcgccca
gggcggggag gaggagtggg acttcgcctg ggagcagttc cgaaatgcca cactggttcaa
tgaggctgac aagctccggg cagccctggc ctgcagcaaa gagttgtgga tcctgaacag
gtacctgagc tacacccctga acccggactt aatccggaag caggacgcca cctctaccat
catcagcatt accaacaacg tcattgggca aggtctggtc tgggactttg tccagagcaa
ctggaagaag ctttttaacg attatggtgg tggctcgttc tccttctcca acctcatcca
ggcagtgaca cgacgattct ccaccagta tgagctgcag cagctggagc agttcaagaa
ggacaacgag gaaacaggct tcggctcagg caccccgggcc ctggagcaag ccctggagaa
gacgaaagcc aacatcaagt gggtgaagga gaacaaggag gtggtgctcc agtggttcac
agaaaacagc aaatagtccc cagccttga gtcacccgg ccccccatgca aggtgcccac
atgtgtccat cccagcggct ggtgcagggc ctccattcct ggagcccgag gcaccagtgt
cctcccctca aggacaaagt ctccagccca cgttctctct gcctgtgagc cagtctagtt
cctgatgacc caggctgcct gagcacctcc cagcccctgc ccctcatgcc aaccccgccc
taggcctggc atggcacctg tcgcccagtg ccctggggct gatctcaggg aagcccagct
ccagggccag atgagcagaa gctctcgatg acaatgaac ggccttgctg ggggccgccc
tgtaccctct ttcacctttc cctaaagacc ctaaatctga ggaatcaaca gggcagcaga
tctgtatatt ttttttctaag agaaatgta aataaaggat ttctagatga aaaaaaaaa
aaaaaaaaaa aaaaaaaaaa aaaaaaaaaa aaaaaaaaaa aaaaaaaaaa aaaaaaaaaa
aaaaaaaaaa aaaaaaaaaa
``` aminopeptidase N precursor [*Homo sapiens*]
NCBI Reference Sequence: NP_001141.2

(SEQ ID NO: 03)

```
MAKGFYISKS LGILGILLGV AAVCTIIALS VVYSQEKNKN ANSSPVASTT PSASATTNPA
SATTLDQSKA WNRYRLPNTL KPDSYRVTLR PYLTPNDRGL YVFKGSSTVR FTCKEATDVI
IIHSKKLNYT LSQGHRVVLR GVGGSQPPDI DKTELVEPTE YLVVHLKGSL VKDSQYEMDS
EFEGELADDL AGFYRSEYME GNVRKVVATT QMQAADARKS FPCFDEPAMK AEFNITLIHP
KDLTALSNML PKGPSTPLPE DPNWNVTEPH TTPKMSTYLL AFIVSEFDYV EKQASNGVLI
RIWARPSAIA AGHGDYALNV TGPILNFFAG HYDTPYPLPK SDQIGLPDFN AGAMENWGLV
TYRENSLLFD PLSSSSSNKE RVVTVIAHEL AHQWFGNLVT IEWWNDLWLN EGFASYVEYL
GADYAEPTWN LKDLMVLNDV YRVMAVDALA SSHPLSTPAS EINTPAQISE LFDAISYSKG
```

TABLE 1-continued

| ANPEP Sequences |
|---|

```
ASVLRMLSSF LSEDVFKQGL ASYLHTFAYQ NTIYLNLWDH LQEAVNNRSI QLPTTVRDIM
NRWTLQMGFP VITVDTSTGT LSQEHFLLDP DSNVTRPSEF NYVWIVPITS IRDGRQQQDY
WLIDVRAQND LFSTSGNEWV LLNLNVTGYY RVNYDEENWR KIQTQLQRDH SAIPVINRAQ
IINDAFNLAS AHKVPVTLAL NNTLFLIEER QYMPWEAALS SLSYFKLMFD RSEVYGPMKN
YLKKQVTPLF IHFRNNTNNW REIPENLMDQ YSEVNAISTA CSNGVPECEE MNSGLFKQWM
ENPNNNPIHP NLRSTVYCNA IAQGGEEEWD FAWEQFRNAT LVNEADKLRA ALACSKELWI
LNRYLSYTLN PDLIRKQDAT STIISITNNV IGQGLVWDFV QSNWKKLFND YGGGSFSFSN
LIQAVTRRFS TEYELQQLEQ FKKDNEETGF GSGTRALEQA LEKTKANIKW VKENKEVVLQ
WFTENSK
```

AMPN_HUMAN Aminopeptidase N enzymatically inactive mutant H392A
(SEQ ID NO: 04)
```
MAKGFYISKSLGILGILLGVAAVCTIIALSVVYSQEKNKNANSSPVASTTPSASATTNPASATTL
DQSKAWNRYRLPNTLKPDSYRVTLRPYLTPNDRGLYVFKGSSTVRFTCKEATDVIIIHSKKLNYT
LSQGHRVVLRGVGGSQPPDIDKTELVEPTEYLVVHLKGSLVKDSQYEMDSEFEGELADDLAGFYR
SEYMEGNVRKVVATTQMQAADARKSFPCFDEPAMKAEFNITLIHPKDLTALSNMLPKGPSTPLPE
DPNWNVTEFHTTPKMSTYLLAFIVSEFDYVEKQASNGVLIRIWARPSAIAAGHGDYALNVTGPIL
NFFAGHYDTPYPLPKSDQIGLPDFNAGAMENWGLVTYRENSLLFDPLSSSSSNKERVVTVIAHEL
AAQWFGNLVTIEWWNDLWLNEGFASYVEYLGADYAEPTWNLKDLMVLNDVYRVMAVDALASSHPL
STPASEINTPAQISELFDAISYSKGASVLRMLSSFLSEDVFKQGLASYLHTFAYQNTIYLNLWDH
LQEAVNNRSIQLPTTVRDIMNRWTLQMGFPVITVDTSTGTLSQEHFLLDPDSNVTRPSEFNYVWI
VPITSIRDGRQQQDYWLIDVRAQNDLFSTSGNEWVLLNLNVTGYYRVNYDEENWRKIQTQLQRDH
SAIPVINRAQIINDAFNLASAHKVPVTLALNNTLFLIEERQYMPWEAALSSLSYFKLMFDRSEVY
GPMKNYLKKQVTPLFIHFRNNTNNWREIPENLMDQYSEVNAISTACSNGVPECEEMVSGLFKQWM
ENPNNNPIHPNLRSTVYCNAIAQGGEEEWDFAWEQFRNATLVNEADKLRAALACSKELWILNRYL
SYTLNPDLIRKQDATSTIISITNNVIGQGLVWDFVQSNWKKLFNDYGGGSFSFSNLIQAVTRRFS
TEYELQQLEQFKKDNEETGFGSGTRALEQALEKTKANIKWVKENKEVVLQWFTENSK
```

AMPN_HUMAN Aminopeptidase N enzymatically inactive mutant H388A
(SEQ ID NO: 05)
```
MAKGFYISKSLGILGILLGVAAVCTIIASLVVYSQEKNKNANSSPVASTTPSASATTNPASATTL
DQSKAWNRYRLPNTLKPDSYRVTLRPYLTPNDRGLYVFKGSSTVRFTCKEATDVIIIHSKKLNYT
LSQGHRVVLRGVGGSQPPDIDKTELVEPTEYLVVHLKGSLVKDSQYEMDSEFEGELADDLAGFYR
SEYMEGNVRKVVATTQMQAADARKSFPCFDEPAMKAEFNITLIHPKDLTALSNMLPKGPSTPLPE
DPNWNVTEFHTTPKMSTYLLAFIVSEFDYVEKQASNGVLIRIWARPSAIAAGHGDYALNVTGPIL
NFFAGHYDTPYPLPKSDQIGLPDFNAGAMENWGLVTYRENSLLFDPLSSSSSNKERVVTVIAAEL
AHQWFGNLVTIEWWNDLWLNEGFASYVEYLGADYAEPTWNLKDLMVLNDVYRVMAVDALASSHPL
STPASEINTPAQISELFDAISYSKGASVLRMLSSFLSEDVFKQGLASYLHTFAYQNTIYLNLWDH
LQEAVNNRSIQLPTTVRDIMNRWTLQMGFPVITVDTSTGTLSQEHFLLDPDSNVTRPSEFNYVWI
VPITSIRDGRQQQDYWLIDVRAQNDLFSTSGNEWVLLNLNVTGYYRVNYDEENWRKIQTQLQRDH
SAIPVINRAQIINDAFNLASAHKVPVTLALNNTLFLIEERQYMPWEAALSSLSYFKLMFDRSEVY
GPMKNYLKKQVTPLFIHFRNNTNNWREIPENLMDQYSEVNAISTACSNGVPECEEMVSGLFKQWM
ENPNNNPIHPNLRSTVYCNAIAQGGEEEWDFAWEQFRNATLVNEADKLRAALACSKELWILNRYL
SYTLNPDLIRKQDATSTIISITNNVIGQGLVWDFVQSNWKKLFNDYGGGSFSFSNLIQAVTRRFS
TEYELQQLEQFKKDNEETGFGSGTRALEQALEKTKANIKWVKENKEVVLQWFTENSK
```

AMPN_HUMAN Aminopeptidase N non-phosphorylatable mutant Y6F
(SEQ ID NO: 06)
```
MAKGFFISKSLGILGILLGVAAVCTIIALSVVYSQEKNKNANSSPVASTTPSASATTNPASATTL
DQSKAWNRYRLPNTLKPDSYRVTLRPYLTPNDRGLYVFKGSSTVRFTCKEATDVIIIHSKKLNYT
LSQGHRVVLRGVGGSQPPDKDKTELVEPTEYLVVHLKGSLVKDSQYEMDSEFEGELADDLAGFYR
SEYMEGNVRKVVATTQMQAADARKSFPCFDEPAMKAEFNITLIHPKDLTALSNMLPKGPSTPLPE
DPNWNVTEFHTTPKMSTYLLAFIVSEFDYVEKQASNGVLIRIWARPSAIAAGHGDYALNVTGPIL
NFFAGHYDTPYPLPKSDQIGLPDFNAGAMENWGLVTYRENSLLFDPLSSSSSNKERVVTVIHELA
HQWFGNLVTIEWWNDLWLNEGFASYVEYLGADYAEPTWNLKDLMVLNDVYRVMAVDALASSHPLS
TPASEINTPAQISELFDAISYSKGASVLRMLSSFLSEDVFKQGLASYLHTFAYQNTIYLNLWDHL
QEAVNNRSIQLPTTVRDIMNRWTLQMGFPVITVDTSTGTLSQEHFLLDPDSNVTRPSEFNYVWIV
PITSIRDGRQQQDYWLIDVRAQNDLFSTSGNEWVLLNLNVTGYYRVNYDEENWRKIQTQLQRDHS
AIPVINRAQIINDAFNLASAHKVPVTLALNNTLFLIEERQYMPWEAALSSLSYFKLMFDRSEVYG
PMKNYLKKQVTPLFIHFRNNTNNWREIPENLMDQYSEVNAISTACSNGVPECEEMVSGLFKQWME
NPNNNPIHPNLRSTVYCNAIAQGGEEEWDFAWEQFRNATLVNEADKLRAALACSKELWILNRYLS
YTLNPDLIRKQDATSTIISITNNVIGQGLVWDFVQSNWKKLFNDYGGGSFSFSNLIQAVTRRFST
EYELQQLEQFKKDNEETGFGSGTRALEQALEKTKANIKWVKENKEVVLQWFTENSK
```

*Mus musculus* alanyl (membrane) aminopeptidase (ANPEP), mRNA
NCBI Reference Sequence: NM_008486.2
(SEQ ID NO: 07)
```
ggcagtgggg ctccaccccc tgtgaggata taagctggcc ccggggctgc tcttctttcc
tcttggcctg agctattccg agctcccctgt ccaccggcat catggccaag gggttctaca
tttccaagac cctgggcatc ttgggcatcc tgttggtgt ggcagctgtg tgtaccatca
tagctctgtc ggtggtctac gctcaggaga agaataggaa tgcagagaac tctgccacag
cccccacgct cccgggcagc acctcagcca ccaccgcaac caccacccct gctgtagatg
aaagccaagc ttggaaccag tatcgcttgc ctaagactct tataccgact tcctaccggg
tgatcctgag accctacctc accccaaca atcagggctg gtacatcttc caaggcaaca
gtactgttcg ctttacctgc aaccagacca cggatgtcat tatcatccac agcaaaaagc
tcaactacac cctcaaagga aaccacaggg tggtgttgcg aacccggac ggcactccgg
cacctaacat tgacaaaacg gaactggtag agcgtactga gtacctggtg gtgcacctgc
aggggtccct ggtagagggc cgtcagtacg agatggacag ccagttccag ggggaactgg
```

TABLE 1-continued

ANPEP Sequences

```
ctgatgacct ggctggcttc taccgcagcg agtacatgga aggagacgtc aagaaagtgg
tggctacaac gcagatgcag gctgctgatg ctcggaaatc ctttccatgt tttgatgagc
cagccatgaa ggccatgttc aacatcacac tcatctaccc caacaacctc atagctctgt
ctaatatgct tcccaaagag tccaagccct atccggaaga cccttcctgc accatgactg
agttccactc caccccctaag atgtccacat acctgctggc ctacatcgtg agcgagttca
aaaatataag ctccgtctca gccaatggtg tccagattgg aatctgggct cggcccagtg
ccattgatga gggccagggt gattacgcac tgaacgttac aggccccatc ctaaatttct
ttgcccaaca ttataataca tcctaccctc taccaaagtc tgaccagatt gccctgcctg
acttcaacgc tggagccatg gagaactggg gtctggtgac ctaccgtgag agctccctgg
tctttgactc tcagtcctcc tccattagca acaaggagcg ggtggtcact gtgattgctc
acgagctggc ccatcagtgg tttggcaacc tggtgactgt ggcttggtgg aatgatctgt
ggctgaacga gggctttgcc tcctacgtgg aatatctggg tgctgactat gcagagccta
cctggaatct gaaagacctc atggtactga atgatgtgta ccgtgtgatg gccgtggatg
cccttgcctc ctcccaccca ctgtccagtc ctgctgacga gatcaaaaca ccagaccaga
tcatggagct gtttgacagc atcacctaca gcaagggagc ctcagtcatc aggatgctgt
ccagtttcct gacagaggac ctgtttaaga agggcctttc atcttatctc cacacctacc
agtactcgaa caccgtttat ctggacctgt gggaacacct gcaaaaggcc gtgaaccaac
agacagctgt ccaacccccg gccacggtgc gcactatcat ggaccgctgg attctacaga
tgggctttcc cgttatcact gtgaacacca atacaggaga aatctcccag aaacacttcc
tcctggattc caagtccaac gttacccgcc cctccgagtt taattacatc tggatcgcgc
ccattccatt tctcaaaagt ggacaggagg atcactactg gctggatgtc gagaaaaacc
agagtgcaaa gttccagaca tcctccaatg aatggattct actgaacatt aacgtaaccg
gctactacct ggttaactat gatgagaaca actggaagaa gcttcagaat cagctgcaaa
cagaccttc tgttatccct gtcatcaacc gagcacagat tatccacgac tccttcaacc
tggcagtgc taaaatgata cccatcaccc tggcgctgga caacccctc ttcctggtca
aagaggcgga gtacatgccc tggcaggctg ccctgagcag cctcaactac ttcacactca
tgttcgaccg ctcggaggtc tacggcccca tgaagaggta tctgaagaag caagttacgc
ccctcttctt ctacttccaa aatagaacca acaactgggt caaccgtcct ccaacgctga
tggagcagta caatgaaatt aacgccatca gcaccgcctg ttccagtggt ctcaaagagt
gtagggacct ggtcgttgag ctctatagtc agtggatgaa aaaccctaat aataacacga
tccaccccaa ccttcggtct actgtctact gcaatgccat tgctttcggt ggcgaagaag
agtggaactt tgcttgggaa cagttccgga atgcaactct ggtgaacgaa gcggacaaac
tccggtcagc cttggcctgt agcaaagatg tgtggatttt gaacaggtac ctgagttaca
ctctgaaccc ggactacatc cggaagcagg acaccacctc caccatcatc agcattgcca
gcaacgtggc tgggcaccct ctggtttggg actttgtccg aagcaactgg aagaaactgt
ttgagaatta cggtggagga tcttttctcct ttgccaatct catccaggga gtgacccggc
gcttctcctc tgagttcgag ctgcagcagc tggagcagtt taaagcggat aactcagcca
caggctttgg caccggcact cgggctctgg agcaagccct ggagaagacg agagccaaca
tcgactgggt gaaggagaac aaagatgcgg tattcaagtg gttcacagag aacagcagtt
agttcctggt tctgagaacc actttgtccca gtatgcacacc tcttactatc tcagcagcct
gtgcagggtc tctgtcctca gagctccaga caccagcatc ctactctcaa ggatgaagtc
tccagcctgt ggagccagcc tagctcctaa ctgtcaggct gacggacacc tcccaggtct
tgcaccctca tgccaactct gccccaggtc caggcctctg gggctgatct cagggaagcc
cagctctgaa gctagattta ctggacaaag ggcagcctgg aaagagactc cctgaatgct
ttactatccc tgccccctac ccccacccct accccccacg agatccgaaa ccaaagaatc
aacagggcac aagatctata tatattttta agagaaaatg taaataaaga atttctaaaa
tgaaaaaaaa aaaaaaaaa
``` aminopeptidase N [Mus musculus]
NCBI Reference Sequence: NP_032512.2

(SEQ ID NO: 08)

```
MAKGFYISKT LGILGILLGV AAGCTIIALS VVYAQEKNRN AENSATAPTL PGSTSATTAT
TTPAVDESKP WNQYRLPKTL IPDSYRVILR PYLTPNNQGL YIFQGNSTVR FTCNQTTDVI
IIHSKKLNYT LKGNHRVVLR TLDGTPAPNI DKTELVERTE YLVVHLQGSL VEGRQYEMDS
QFQGELADDL AGFYRSEYME GDVKKVVATT QMQAADARKS FPCFDEPAMK AMFNITLIYP
NNLIALSNML PKESKPYPED PSCTMTEFHS TPKMSTYLLA YIVSEFKNIS SVSANGVQIG
IWARPSAIDE GQGDYALNVT GPILNFFAQH YNTSYPLPKS DQIALPDFNA GAMENWGLVT
YRESSLVFDS QSSSISNKER VVTVIAHELA HQWFGNLVTV AWWNDLWLNE GFASYVEYLG
ADYAEPTWNL KDLMVLNDVY RVMAVDALAS SHPLSSPADE IKTPDQIMEL FDSITYSKGA
SVIRMLSSFL TEDLFKKGLS SYLHTYQYSN TVYLDLWEHL QKAVNQQTAV QPPATVRTIM
DRWILQMGFP VITVNTNTGE ISQHKFLLDS KSNVTRPSEF NYIWIAPIPF LKSGQEDHYW
LDVEKNQSAK FQTSSNWEIL LNINVTGYYL VNYDENNWKK LQNQLQTDLS VIPVINRAQI
IHDSFNLASA KMIPITLALD NTLFLVKEAE YMPWQAALSS LNYFTLMFDR SEVYGPMKRY
LKKQVTPLFF YFQNRTNNWV NRPPTLMEQY NEINAISTAC SSGLKECRDL VVELYSQWMK
NPNNNTIHPN LRSTVYCNAI AFGGEEEWNF AWEQFRNATL VNEADKLRSA LACSKDVWIL
NRYLSYTLNP DYIRKQDTTS TIISIASNVA GHPLVWDFVR SNWKKLFENY GGGSFSFANL
IQGVTRRFSS EFELQQLEQF KADNSATGFG TGTRALEQAL EKTRANIDWV KENKDAVFKW
FTENSS
```

The inhibitor can prevent the expression, activity and/or function of ANPEP; any suitable ANPEP inhibitor can be used, as deemed most appropriate for an intended use. In exemplary embodiments, the inhibitor can be selected from the group consisting of anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides and small molecule ANPEP inhibitors. In a preferred embodiment, the inhibitor is an anti-ANPEP antibody (i.e., an antibody that binds to ANPEP).

As used herein, the term "subject" or "patient" is meant to include any subject for which a donor transplant or donor or treatment may be required. "Subjects" or "patients" can comprise both humans and non-humans and includes; but is not limited to, humans, monkeys, cattle, dogs, cats, guinea pigs, rabbits, rats, mice, insects, horses, chickens, and so on. Most preferably, the subject is human. In some embodiments, the subject or patient may regime a graft or transplant due to a congenital defect (e.g., congenital anomaly of the heart, limbs or kidneys), traumatic injury, acquired allergic reactions or disease sequelae (e.g., chronic kidney disease can be a sequel of diabetes). In an exemplary embodiment, a patient born with a congenital heart defect can receive a new heart or heart tissue with no defect created with the pluripotent cells that lack ANPEP expression. In another embodiment, tissues such as skin, muscle or nerve can be created and stored in hospitals for the immediate transplant into trauma patients. In yet another embodiment, therapeutic cells that produce insulin or mast cell stabilizers can be created from pluripotent cells lacking ANPEP expression and transplanted into diabetes patients or patients suffering from allergic airway disease and asthma. In embodiments where the immune system should be enhanced instead of suppressed, such as in cancer patients, CD13 inhibition would not be used; rather, CD13 function will be enhanced to exert the corresponding effects on immunity.

Transplant rejection occurs when transplanted tissue is rejected by the recipient's immune system, which destroys the transplanted tissue. Transplant rejection can be lessened by determining the molecular similarity between donor and recipient and by use of immunosuppressant drugs before and after the transplant procedure. Immune cells from the subject receiving the donor transplant or donor graft recognize the donor transplant or donor graft as "foreign". The recipient's immune cells then attack the transplanted donor transplant or donor graft which can result in transplant rejection. In addition, residual immune cells in the donor transplant or donor graft can mobilize to a recipient's peripheral lymphoid organs and initiate graft versus host disease, attacking host cells and causing extensive damage. The methods and compositions of the invention can prevent transplant rejection by mitigating or eliminating the immune reactions of the recipient to the donor transplant or donor graft.

As used herein, "treating transplant rejection" or "limiting development of transplant rejection" means accomplishing one or more of the following: 1) reducing the severity of an immune response to a donor transplant or donor graft; 2) inhibiting or preventing development of an immune response at the donor transplant or graft location; 3) inhibiting or preventing the worsening of an immune response at the donor transplant or graft location; or 4) inhibiting or preventing the development of immune-mediated complications ultimately resulting in rejection of the donor transplant or graft.

In an embodiment, the subject receiving a donor transplant is treated with an ANPEP inhibitor before the transplant procedure occurs. The inhibitor can be administered to the subject one day, two days, three days, four days five days, six days, one week, two weeks, three weeks, four week or more before the transplant procedure; and continued to be administered for one week, two weeks, three weeks, one month, two months, three months or more after the transplant procedure as necessary in order to prevent transplant rejection. In another embodiment, the donor transplant is treated with an ANPEP inhibitor for the transplant procedure. The inhibitor can be administered to the donor transplant one day, two days, three days, four days five days, six days, one week, two weeks, three weeks, four week or more before the transplant procedure; and continued to be administered for one week, two weeks, three weeks, one month, two months, three months or more after the transplant procedure as necessary in order to prevent transplant rejection. In some embodiments, both the subject receiving the donor transplant and the donor transplant are treated with an ANPEP inhibitor. In such cases, the inhibitor can be administered to the subject and donor transplant one day, two days, three days, four days five days, six days, one week, two weeks, three weeks, four week or more before the transplant procedure; and continued to be administered for one week, two weeks, three weeks, one month, two months, three months or more after the transplant procedure as necessary in order to prevent transplant rejection.

As used herein, the term "donor transplant" or "donor graft" refers to a population of cells, or a tissue or an organ that is to be moved from one body to another or from a donor site to another location on the subject's own body, for the purpose of replacing the recipient's damaged or absent tissue or organ. In some embodiments, the donor transplant can be re-grown from the patient's own cells (e.g., pluripotent cells or stem cells, or cells extracted from the failing organs). In other embodiments, the donor transplant or graft can be grown from a pluripotent cell population lacking ANPEP, as described herein.

The donor transplant or graft may be a cell, tissue, or organ, as is suitable for an intended use. Exemplary donor transplants or grafts can be selected from, but are not limited to: skin cells, beta cells (i.e., cells in the pancreas located in the islets of Langerhans), cardiac cells, brain cells, kidney cells, liver cells, cells of the digestive tract and accessory digestive organs, salivary gland cells, adrenal gland cells, prostate cells, lung cells, pancreatic cells, bone cells, immune cells, hematopoietic cells, vascular cells, cells of the eye, connective tissue cells, musculoskeletal cells, bone tissue, musculoskeletal tissue, cornea tissue, skin tissue, heart valves, blood vessels, immune cells, connective tissue, lung tissue, skin, a cornea, a kidney, a liver, a lung, a pancreas, a heart, and intestine, in preferred embodiments, the donor graft is comprised of skin cells, skin tissue or beta-cells.

The cell, tissue and/or organ to be transplanted can be syngeneic, allogenic or xenogenic to the subject receiving the transplant. As used herein, the term "syngic" or "syngeneic" refers to cells, tissues or organs that are genetically identical or are derived from a genetically identical source to the transplant recipient (e.g., an identical twin), especially with respect to antigens or immunological reactions. Such cells, tissues or organs are called isografts. As used herein, the term "allogenic" or "allogeneic" refers to cells, tissues or organs that are not genetically identical or are derived from a non-genetically identical source to the transplant recipient (e.g., a non-related donor), especially with respect to antigens or immunological reactions. Such cells, tissues or organs are called allografts, allogeneic transplants, homografts or allotransplants. As used herein, the term "xenogenic" or "xenogeneic" refers to cells, tissues or organs that are from a different species to the transplant recipient (e.g., a pig donor to a human recipient), especially with respect to antigens or immunological reactions. Such cells, tissues or organs are called xenografts or xenotransplants.

In another embodiment, the invention provides a method of reducing an immune response comprising administering to a subject in need thereof with an effective amount of an inhibitor of alanyl (membrane) aminopeptidase (ANPEP) to reduce an immune response. In an embodiment, the subject in need thereof is a subject with an autoimmune condition, an immune hyper-reactive condition, a chronic inflammatory condition, or is in need of a transplant. An autoimmune condition can include, but is not limited to, alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, some forms of thyroiditis, some forms of uveitis, vitiligo or granulomatosis with polyangiitis (Wegener's). Immune hyper-reactive conditions can include, but are not limited to, allergies, asthma, eczema or chronic fatigue syndrome. Chronic inflammatory conditions can include, but are not limited to appendicitis, bursitis, colitis, cystitis, dermatitis, phlebitis, rhinitis, tendonitis, tonsillitis or vasculitis.

The subject or the donor transplant or graft may be treated with the inhibitor in any suitable manner (i.e., in vitro; ex vivo; in vivo) to inhibit expression, activity and/or function of ANPEP. As used herein, an "inhibitor" of expression, activity and/or function of ANPEP includes compounds that block the function, peptidase activity and/or signaling of ANPEP, compounds that reduce or prevent the transcription of ANPEP DNA into RNA, compounds that reduce or prevent the translation of ANPEP RNA into protein, and compounds that reduce or prevent the function of ANPEP protein. Such inhibiting can be complete inhibition or partial inhibition, such that the expression and/or activity of ANPEP is reduced, resulting in a reduced protease activity, adhesion or signaling, and prevention of limitation of receptor-mediated antigen uptake and presentation in dendritic cells and regulation of endocytosis and innate immune regulation in any cell type. Such inhibitors are selected from the group consisting of: antibodies that bind to ANPEP; aptamers that can interfere with ANPEP; antisense oligonucleotides directed against the ANPEP DNA or mRNA; small interfering RNAs (siRNAs), short hairpin RNAs (shRNAs), microRNAs (miRNA) or small internally segmented interfering RNAs (sisiRNA) directed against ANPEP protein. DNA, or mRNA, small molecule ANPEP inhibitors and any other chemical or biological compound that can interfere with ANPEP activity. The inhibitor can be used alone or together with other agents as an immunosuppressant to decrease the activity of the immune system, and may prevent transplant rejection or graft-versus-host disease.

When the inhibitor comprises an antibody, such antibodies can be polyclonal or monoclonal. The antibodies can be humanized, fully human, or murine forms of the antibodies. Such antibodies can be made by well-known methods, such as described in Harlow and Lane, Antibodies; A Laboratory Manual, Cold Spring Harbor Laboratory, Cold Spring Harbor. N.Y., (1988). In some embodiments, additional amino acid residues may be added to either the N- or C-terminus of the antibody or antibody fragment. When the inhibitor comprises an aptamer, such aptamers can be oligonucleic acid or peptide molecules that bind to a specific target molecule. Methods of constructing and determining the binding characteristics of aptamers are well known in the art, and the aptamers can be isolated from random libraries or they can be previously identified peptides. When the inhibitor comprises antisense oligonucleotides, such antisense oligonucleotides can be small interfering RNAs (siRNAs), short hairpin RNAs (shRNAs), microRNAs (miRNA) or small internally segmented interfering RNAs (sisiRNA). Methods of constructing and determining the binding characteristics of antisense oligonucleotides are well known in the art, and the antisense oligonucleotides can be designed using known programs or they can be previously identified antisense oligonucleotides.

Administering of ANPEP inhibitors to a subject in need can be via any suitable route as deemed appropriate for an intended use. In certain embodiments, the inhibitor, as described herein, can be administered alone. In certain embodiments, the inhibitor can be administered prior to the administration of at least one other therapeutic agent. In certain embodiments, the inhibitor can be administered concurrent with the administration of at least one other therapeutic agent. In certain embodiments, the inhibitor can be administered subsequent to the administration of at least one other therapeutic agent. In other embodiments, the inhibitor can be administered prior to the administration of at least one other therapeutic agent. As will be appreciated by one of skill in the art, in some embodiments, the inhibitor can be combined with the other agent/compound. In some embodiments, the inhibitor and other agent can be administered concurrently. In some embodiments, the inhibitor and other agent are not administered simultaneously, with inhibitor being administered before or after the agent is administered. In some embodiments, the subject receives both the inhibitor and the other agent during a same period of prevention, occurrence of a disorder, and/or period of treatment.

The methods and cells of the disclosure can be used for a wide variety of pharmaceutical, cosmetic, and medicinal purposes that are known in the art.

In some embodiments, an inhibitor of ANPEP or pharmaceutical compositions comprising an inhibitor of ANPEP can be administered in combination therapy, i.e., combined with other agents. In certain embodiments, the combination therapy comprises the inhibitor, in combination with at least one other agent. Agents include other immunosuppressive agents, but are not limited to corticosteroids and glucocorticoids (e.g., cortisol, hydrocortisone, cortisone, prednisone, prednisolone, methylprednisolone, dexamethasone, betamethasone, triamcinolone, beclometasone, fludrocortisone acetate, deoxycorticosterone acetate or aldosterone), calcineurin inhibitors and drugs acting on immunophilins (e.g., cyclosporine or tacrolimus), mTOR inhibitors (e.g., everolimus or sirlumus), antiproliferative drugs (e.g., azathioprine, cyclophosphamide, mycophenolic acid, mycophenolate mofetil, mizoribine. Additional agents may also include, but are not limited to antibodies or biologics, such as anti-CD3 antibodies, anti-CD20 antibodies, anti-IL2 antibodies, anti-PD-1 antibodies, anti-CTLA4 antibodies or other immunosuppressive agents.

In certain embodiments, the invention provides for pharmaceutical compositions comprising the inhibitor and a therapeutically effective amount of at least one additional therapeutic agent, together with a pharmaceutically acceptable diluent, carrier, solubilizer, emulsifier, preservative and/or adjuvant.

In certain embodiments, acceptable formulation materials preferably are nontoxic to recipients at the dosages and concentrations employed. In some embodiments, the formulation material(s) are for sub-cutaneous (s.c.) and/or intravenous (I.V.) administration. In certain embodiments, the inhibitor of ANPEP or pharmaceutical composition comprising an inhibitor of ANPEP can contain formulation materials for modifying, maintaining or preserving, for example, the pH, osmolarity, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogensulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine; sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In some embodiments, the formulation comprises PBS; 20 mM NaOAC, pH 5.2, 50 mM NaCl; and/or 10 mM NAOAC, pH 5.2, 9% Sucrose.

In certain embodiments, the optimal pharmaceutical composition comprising an ANPEP inhibitor will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and rate of in vivo clearance of the antibodies of the invention.

In certain embodiments, the primary vehicle or carrier of an inhibitor of ANPEP or pharmaceutical compositions comprising an inhibitor of ANPEP can be either aqueous or non-aqueous in nature. For example, in certain embodiments, a suitable vehicle or carrier can be water for injection; physiological saline solution or artificial cerebrospinal fluid, possibly supplemented with other materials common in compositions for parenteral administration. In some embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore.

In certain embodiments, the effective amount of an inhibitor of ANPEP or pharmaceutical compositions comprising an inhibitor of ANPEP as described herein, with or without at least one additional therapeutic agent, to be employed therapeutically will depend, for example, upon the therapeutic context and objectives. One skilled in the art will appreciate that the appropriate dosage levels for treatment, according to certain embodiments, will thus vary depending, in part, upon the inhibitor delivered, the indication for which an inhibitor described herein, with or without at least one additional therapeutic agent, is being used, the route of administration, and the size (body weight, body surface or organ size) and/or condition (the age and general health) of the patient. In certain embodiments; the clinician can titer the dosage and modify the route of administration to obtain the optimal therapeutic effect. In certain embodiments, a typical dosage comprising an antibody that binds to and inhibits ANPEP can range from about 0.1 µg/kg to up to about 100 mg/kg or more, depending on the factors mentioned above. In certain embodiments, the dosage can range from 0.1 µg/kg up to about 100 mg/kg; or 1 µg/kg up to about 100 mg/kg; or 5 µg/kg up to about 100 mg/kg.

In certain embodiments, the frequency of dosing will take into account the pharmacokinetic parameters of the inhibitor described herein and/or any additional therapeutic agents in the formulation used. In certain embodiments, a clinician will administer the composition until a dosage is reached that achieves the desired effect. In certain embodiments, the composition can therefore be administered as a single dose, or as two or more doses (which may or may not contain the same amount of the desired fusion protein) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the inhibitor of ANPEP or pharmaceutical compositions comprising an inhibitor of ANPEP is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device.

In certain embodiments, the inhibitor of ANPEP or pharmaceutical compositions comprising an inhibitor of ANPEP can be administered locally via implantation of a membrane, sponge or another appropriate material onto which the desired inhibitor has been absorbed or encapsulated. In certain embodiments, where an implantation device is used, the device can be implanted into any suitable tissue or organ, and delivery of the desired fusion protein can be via diffusion, timed-release bolus, or continuous administration.

In a second aspect the invention provides a pluripotent cell population, wherein the population does not express functional ANPEP. Functional ANPEP can be knocked out or inhibited by a method selected from the group consisting of generation of knock-in null mutant ANPEP cell population using homologous recombination, generation of knock-in null mutant ANPEP cell population using transcription activator-like effector nucleases (TALENs), generation of knock-in null mutant ANPEP cell population using clustered regularly interspaced short palindromic repeats (CRISPR) technology generation of ANPEP knockout cell fine using homologous recombination, generation of ANPEP knockout cell lines using TALEN, generation of ANPEP knockout cell lines using CRISPR technology, generation of ANPEP mutant cell lines using homologous recombination, generation of ANPEP mutant cell lines using TALEN, generation of ANPEP mutant cell lines using CRISPR technology, anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides and small molecule ANPEP inhibitors.

As used herein, the term "pluripotent cell population" refers to animal, especially mammalian, preferably human, pluripotent cells. Pluripotent cells refer to unspecialized cells that have the ability to self-renew for long periods of time and differentiate into specialized cells with specific functions. Pluripotent cells can refer to stem cells that have the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues and nervous system). Cell pluripotency can be a continuum, ranging from the pluripotent cell that can form every cell of the embryo proper, e.g., embryonic stem cells and induced pluripotent stem cells, to the incompletely or partially pluripotent cell that can form cells of all three germ layers, but that may not exhibit all the characteristics of completely pluripotent cells. Pluripotent cells can refer to progenitor cells which have the gene activation potential to differentiate into multiple, but limited cell types. For example, a pluripotent blood stem cell is a hematopoietic cell and this cell type can differentiate itself into several types of blood cell types like lymphocytes, monocytes, or neutrophils, but cannot differentiate into brain cells, bone cells or other non-blood cell types. Pluripotent cells can be found in many, but not all human cell types (for example, pluripotent cells have been found in adipose tissue, cardiac cells, bone marrow, and mesenchymal stromal cells).

As used herein, the term "functional ANPEP" refers to ANPEP protein with both enzyme-dependent and independent functions that contribute to adhesion, cell migration, angiogenesis, inflammatory trafficking, adhesion, antigen presentation, and endocytosis. In an embodiment, the cells, tissues and organs of the invention lacking functional ANPEP can have endogenous ANPEP knocked-out of the cell, tissue or organ or expression can be disrupted at transcription or translation step and therefore the cell, tissue or organ therefore does not express ANPEP. In another embodiment, the cells, tissues or organs of the invention lacking functional ANPEP can have endogenous ANPEP replaced by knock-in of a mutant ANPEP that does not function properly and therefore ANPEP cannot contribute to adhesion, cell migration, angiogenesis, inflammatory trafficking, adhesion, antigen presentation, and endocytosis. In yet another embodiment, the cells, tissues or organs of the invention lacking functional ANPEP can have endogenous ANPEP inhibited and therefore ANPEP cannot contribute to adhesion, cell migration, angiogenesis, inflammatory trafficking, adhesion, antigen presentation, and endocytosis.

In an embodiment, the invention provides a pluripotent cell population in which functional ANPEP has been knocked out or inhibited by a method selected from the group consisting of: generation of knock-in null mutant ANPEP cell population using homologous recombination, generation of knock-in null mutant ANPEP cell population using TALEN, generation of knock-in null mutant ANPEP cell population using CRISPR technology, generation of ANPEP knockout cell lines using homologous recombination, generation of ANPEP knockout cell lines using TALEN, generation of ANPEP knockout cell lines using CRISPR technology, generation of ANPEP mutant cell lines using homologous recombination, generation of ANPEP mutant cell lines using TALEN, generation of ANPEP mutant cell lines using CRISPR technology, anti-ANPEP antibody, anti-ANPEP aptamer, ANPEP small interfering RNA, ANPEP small internally segmented interfering RNA, ANPEP short hairpin RNA, ANPEP micro RNA, small molecule inhibitors of ANPEP and ANPEP antisense oligonucleotides. CRISPR/Cas-based RNA-guided DNA endonucleases are genome editing tools (Wang et al., 2013 "One-Step Generation of Mice Carrying Mutations in Multiple Genes by CRISPR/Cas-Mediated Genome Engineering." *Cell* 153(4):910-18). Transcription activator-like effector nucleases (TALENs) comprise chimeric nucleases that are composed of programmable, sequence-specific DNA-binding modules linked to a nonspecific DNA cleavage domain. TALENs enable a broad range of genetic modifications by inducing DNA double-strand breaks that stimulate error-prone nonhomologous end joining or homology-directed repair at specific genomic locations (Gaj et al., 2013 "ZFN, TALEN, and CRISPR/Cas-based methods for genome engineering." *Trends Biotechnol.* 31(7):397-405).

In another embodiment, the invention provides a differentiated population of cells for transplanting into a subject in need thereof, wherein the cells are derived from the pluripotent cells lacking functional ANPEP. The differentiated population of cells can be selected from the group consisting of: skin cells, beta cells, cardiac cells, brain cells, kidney cells, liver cells, cells of the digestive tract and accessory digestive organs, salivary gland cells, adrenal gland cells, prostate cells, lung cells, pancreatic cells, bone cells, immune cells, hematopoietic cells, vascular cells, cells of the eye, connective tissue cells and musculoskeletal cells. In a preferred embodiment, the cells are skin cells or beta cells lacking functional ANPEP.

The differentiated population of cells can be derived from the pluripotent cells lacking functional ANPEP by a number of protocols that are already developed or are currently being optimized by others in the field. These methods can include, but are not limited to, systematic induction of differentiation using special cell culture matrices, media and growth factor or small molecule supplements administered in specific time windows that mimic normal developmental timepoints, introduction of certain genes and growth factors or cytokines into cells to promote immediate switching of cell types, or the in vivo introduction of certain genes, growth factors or cytokines into cells to promote endogenous differentiation of cells.

In yet another embodiment, the invention provides a tissue for transplanting into a subject in need thereof, wherein the tissue is derived from the pluripotent cell population lacking functional ANPEP. The tissue can be selected from the group consisting of: bone tissue, musculoskeletal tissue, cornea tissue, skin tissue, heart valves, and blood vessels, immune cells, connective tissue, lung tissue. In a preferred embodiment, the tissue is skin tissue lacking functional ANPEP.

The differentiated tissue can be derived from the pluripotent cells lacking functional ANPEP by a number of protocols that are already developed or are currently being optimized by others in the field. These methods can include, but are not limited to, systematic induction of differentiation using special cell culture matrices, media and growth factor or small molecule supplements administered in specific time windows that mimic normal developmental timepoints, introduction of certain genes and growth factors or cytokines into cells to promote immediate switching of cell types, or the in vivo introduction of certain genes, growth factors or cytokines into cells to promote endogenous differentiation of cells. Cells generated in vitro can be seeded onto bioengineered scaffolds that can provide the three dimensional structure of the tissue of interest. These scaffolds can be created by three dimensional printing with biomaterials specifically developed for these purposes, including but not limited to, synthetic materials, protein based materials and polysaccharide based materials, such as polyglycolic acid, polylactic acid, fibrin, glycosaminoglycans.

In a further embodiment, the invention provides an organ for transplanting into a subject in need thereof, wherein the organ is derived from the pluripotent cell population lacking functional ANPEP. The organ can be selected from, but is not limited to, the group consisting of: cornea, skin, kidney, liver, lung, heart, pancreas and intestine. In a preferred embodiment, the organ is skin lacking functional ANPEP.

The differentiated organ can be derived from the pluripotent cells lacking functional ANPEP by a number of protocols that are already developed or are currently being optimized by others in the field. These methods can include, but are not limited to, systematic induction of differentiation using special cell culture matrices, media and growth factor or small molecule supplements administered in specific time windows that mimic normal developmental timepoints, introduction of certain genes and growth factors or cytokines into cells to promote immediate switching of cell types, or the in vivo introduction of certain genes, growth factors or cytokines into cells to promote endogenous differentiation of cells. Differentiated cells or stem cells can be seeded onto bioengineered scaffolds to promote further development of a complete organ with the various different cell types and organization that is associated with the particular organ of interest. Bioengineered scaffolds can be created through three dimensional printing with biomaterials or decellularization of existing organs according to protocols optimized by experts in that field. In an alternative method, pluripotent stem cells can be used to generate large multidimensional organoids according to culture methods currently being developed by other experts in the field.

In an another embodiment, the invention provides cells, tissues or organs for transplanting into a subject in need thereof, wherein the cells, tissues or organs are derived from the pluripotent cell population lacking functional ANPEP and also comprise at least one additional modification. In some embodiments, an additional modification can be the genetic engineering of the cells, tissues or organs lacking functional ANPEP to express a gene or peptide. In such an embodiment, the donor transplant can also serve as a means for administering therapeutic proteins and peptides. The peptide is not limited to any particular peptide, but can include any peptide that can be used to treat any number of diseases, disorders or conditions. For example, the therapeutic peptide can include, but is not limited to, nesiritide, ceruletide, bentiromide, exenatide, gonadorelin, enfuvirtide, vancomycin, icatibant, secretin, leuprolide, glucagon recombinant, oxytocin, sermorelin, gramicidin D, insulin, capreomycin, calcitonin, vasopressin, cosyntropin, bacitracin, octreotide, abarelix, vapreatide, thymalfasin, mecasermin, cetrorelix, teriparatide, corticotropin or pramlintide.

In an additional embodiment, the invention provides a method of transplanting cells, tissues and/or organs into a subject in need thereof comprising: pre-treating the cells, tissues and/or organs with ANPEP inhibitors prior to transplanting the cells, tissues and/or organs lacking or blocking functional ANPEP into a subject in need thereof or treating the subject with ANPEP inhibitors prior to transplant. The cell, tissue and/or organ to be transplanted can be syngeneic, allogeneic or xenogeneic to the subject receiving the transplant.

As used herein, the term "syngenic" or "syngeneic" refers to cells, tissues or organs that are genetically identical or are derived from a genetically identical source to the graft recipient (e.g., an identical twin), especially with respect to antigens or immunological reactions. Such cells, tissues or organs are called isografts.

As used herein, the term "allogenic" or "allogeneic" refers to cells, tissues or organs that are not genetically identical or are derived from a non-genetically identical source to the graft recipient (e.g., a non-related donor), especially with respect to antigens or immunological reactions. Such cells, tissues or organs are called allografts, allogeneic transplants, homografts or allotransplants As used herein, the term "xenogenic" or "xenogeneic" refers to cells, tissues or organs that are from a different species to the graft recipient (e.g., a pig donor to a human recipient), especially with respect to antigens or immunological reactions. Such cells, tissues or organs are called xenografts or xenotransplants.

EXAMPLES

The Examples that follow are illustrative of specific embodiments of the invention, and various uses thereof. They are set forth for explanatory purposes only, and are not to be taken as limiting the invention.

Example 1

ANPEP Expression and the Immune Response

To determine the role of ANPEP in immune responses elicited by stem cell transplantation, mouse embryonic stem (mES) cells were derived from ANPEP WT and ANPEP KO mice. These cells proliferate at similar rates and express characteristic pluripotency markers in vitro. When implanted into syngeneic mice, mES of both genotypes form teratomas that contain cell types representing all three embryonic germ layers, demonstrating pluripotency in vivo as well. Surprisingly, teratomas generated from ANPEP KO mES grow more rapidly, achieve a larger size, and show a higher degree of differentiation than those generated from ANPEP WT mES cells. Analysis of potential underlying causes showed that ANPEP KO teratomas contained fewer infiltrating T-lymphocytes and dendritic cells, indicating that lack of ANPEP expression may permit stem cells to escape immune detection and allow Implants to thrive. In agreement with this hypothesis, growth and differentiation of WT and ANPEP KO mES Implanted into immunocompromised mice were comparable, consistent with an underlying immune mechanism. Consequently, modulation of ANPEP expression may alter immune responses toward implanted stem cells and enhance their engraftment to ultimately facilitate repair.

Example 2

Assessment of ANPEP Expression and Immunomodulation

To study the immunomodulatory effects of ANPEP further, the inventors have been studying skin grafts between ANPEP WT and ANPEP KO mice with gender or major histocompatibility-mismatches. Surprisingly, the skin graft studies confirm the observations with the teratomas. ANPEP KO female skin engrafts successfully on both ANPEP WT and ANPEP KO male mice, while ANPEP WT female skin is rejected from both ANPEP WT and ANPEP KO male mice after 14 days.

Comparison of histological sections at sites of engraftment shows that there is significant inflammation and disruption of normal skin architecture in ANPEP WT skin grafts. There is only mild inflammation in ANPEP KO skin engrafted in ANPEP WT mice, while there is virtually no disruption of ANPEP KO skin engrafted in ANPEP KO mice. These studies provide surprising and important evidence that immunological tolerance can be engendered through ANPEP blockade.

Example 3

Skin Grafts Lacking CD13 Survive Longer with Diminished Inflammation

Initial characterization of mice lacking CD13 expression on a global level demonstrated no notable developmental deficiencies or defects in homeostatic processes (Winnicka et al. 2010). However, while site-specific mechanisms influenced specific outcomes, the inflammatory responses of CD13-null animals were universally compromised upon challenge in various injury models (Pereira et al. 2013, Rahman et al. 2013, Subramani et al. 2013, Ghosh et al. 2014). Based on these observations, it was determined if the diminished inflammatory responses seen in CD13-null mice could potentially extend to the inflammatory reactions mediating transplant rejection. Using wild type and global CD13-null mice in a standard model of minor histocompatibility (MiHC) mismatched allograft rejection (FIG. 6), long-term survival of full-thickness CD13-null male donor skin grafts was observed on female recipients that survived for over 100 days (FIG. 1A). The CD13-null grafts maintained their original size as compared to WT skin grafts that wither and gradually shrink in diameter until fully rejected between two to three weeks post-transplant (FIG. 1B). Furthermore, the CD13-null grafts retained the characteristic thin, vascularized skin of the donor dorsal ear and did not adopt the thick fur of the host dorsal skin, suggesting that CD13 can be a potential instigator of allograft rejection. Indeed, while there is evidence of inflammatory cell infiltration into CD13-null graft tissue after one week, the number of cells and the extent of tissue damage was significantly less than that observed in WT skin grafts (FIG. 1C).

Figure 7:
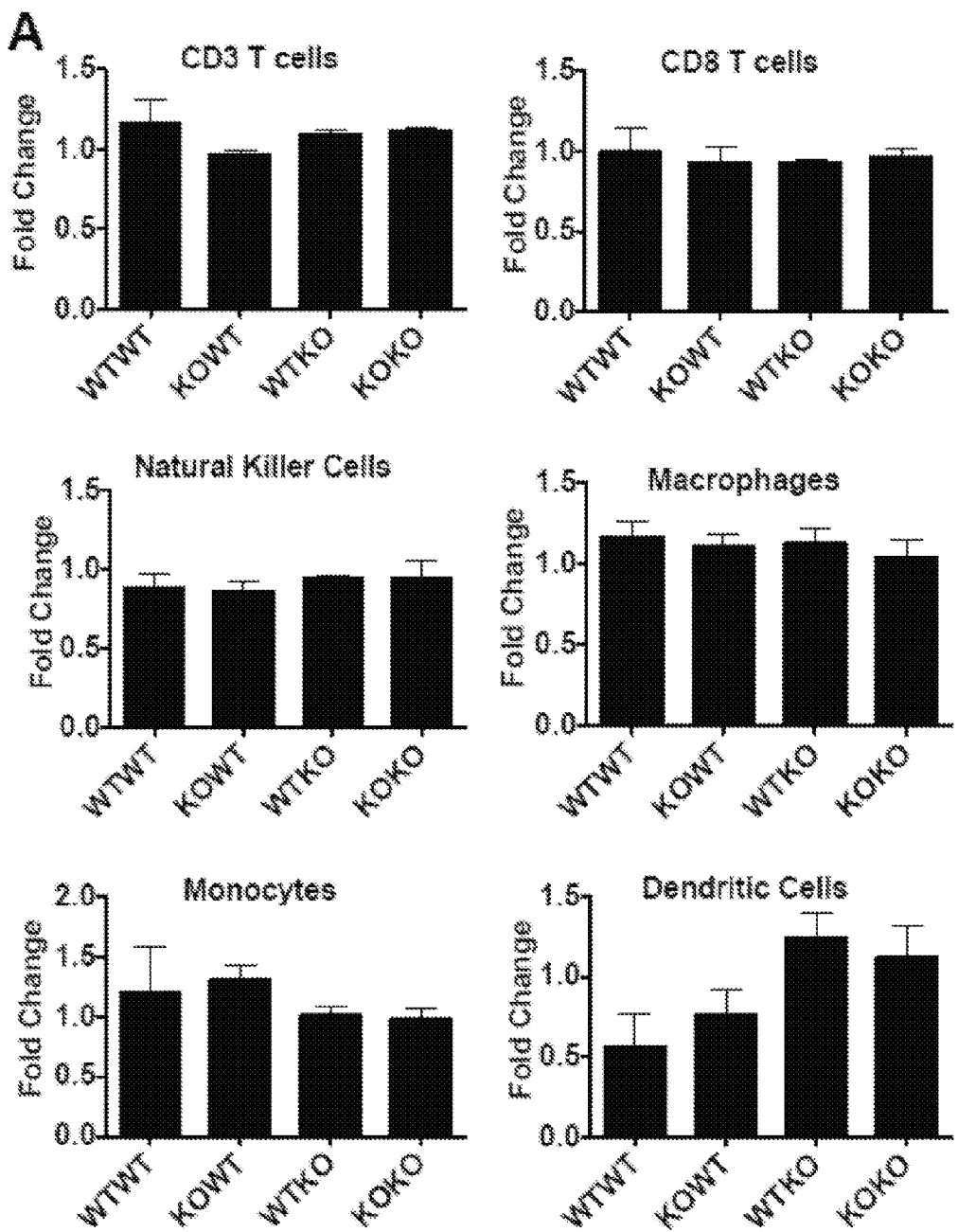
FIG. 7 shows (A) Flow cytometry for immune cell populations in post-transplant Day 5 spleen.

Immunohistochemical quantification of CD3 positive cells in grafts at five days post-transplant indicated that significantly more T cells infiltrated into WT grafts as compared in CD13-null grafts in both WT and CD13-null recipients (FIG. 1D). Flow cytometric analyses of host spleens receiving grafts of either genotype at days 5 and 100 post-transplant indicated that there were no significant differences in various splenic immune populations (FIG. 7) implying that the differences in graft acceptance observed were most likely due to local events in the graft and draining lymph nodes.

Example 4

Mast Cell-mediated Inflammation is Reduced in CD13-null Grafts

Mast cells are traditionally considered pro-inflammatory mediators of the acute immune response; however, recent studies have elucidated novel anti-inflammatory roles for these cells particularly in the setting of allograft survival (Galli et al. 2005, Lu et al. 2006), where mast cells have been shown to be critical for graft survival and their degranulation reverses tolerance to skin allografts (Lu et al. 2006, de Vries et al. 2009). Pertinent to this study, mast cells are known to express high levels of CD13, but the functional role of CD13 in mast cell activity has yet to be demonstrated. To determine the contribution of mast cells to this model of allograft survival, WT and CD13-null skin grafts were examined for the presence of mast cells and their degranulation status using toluidine blue to stain mast cell-specific granular contents. Interestingly, higher levels of toluidine blue staining was observed in CD13-null graft tissue, potentially due to reduced mast cell degranulation in the absence of CD13 (FIGS. 2A and 2B). This increase in granule staining was also seen in the draining lymph nodes, but not the spleens of mice that received CD13-null skin grafts (FIG. 2C). Orthotopic applications of gender mismatched dermal fibroblasts survive longer when mixed with CD13-null mast cells. These results confirm the histological observations that inflammation is reduced in the absence of CD13. Furthermore, given that mast cells are known to produce IL-4, a known stimulator of reparative M2 macrophages, and IL-10, a potent immunosuppressor, it is possible that the diminished inflammation and elevated number of alternatively activated macrophages in CD13-null grafts (FIG. 1F) can be attributed to a degranulation-independent anti-inflammatory function of mast cells.

Example 5

Figure 3:
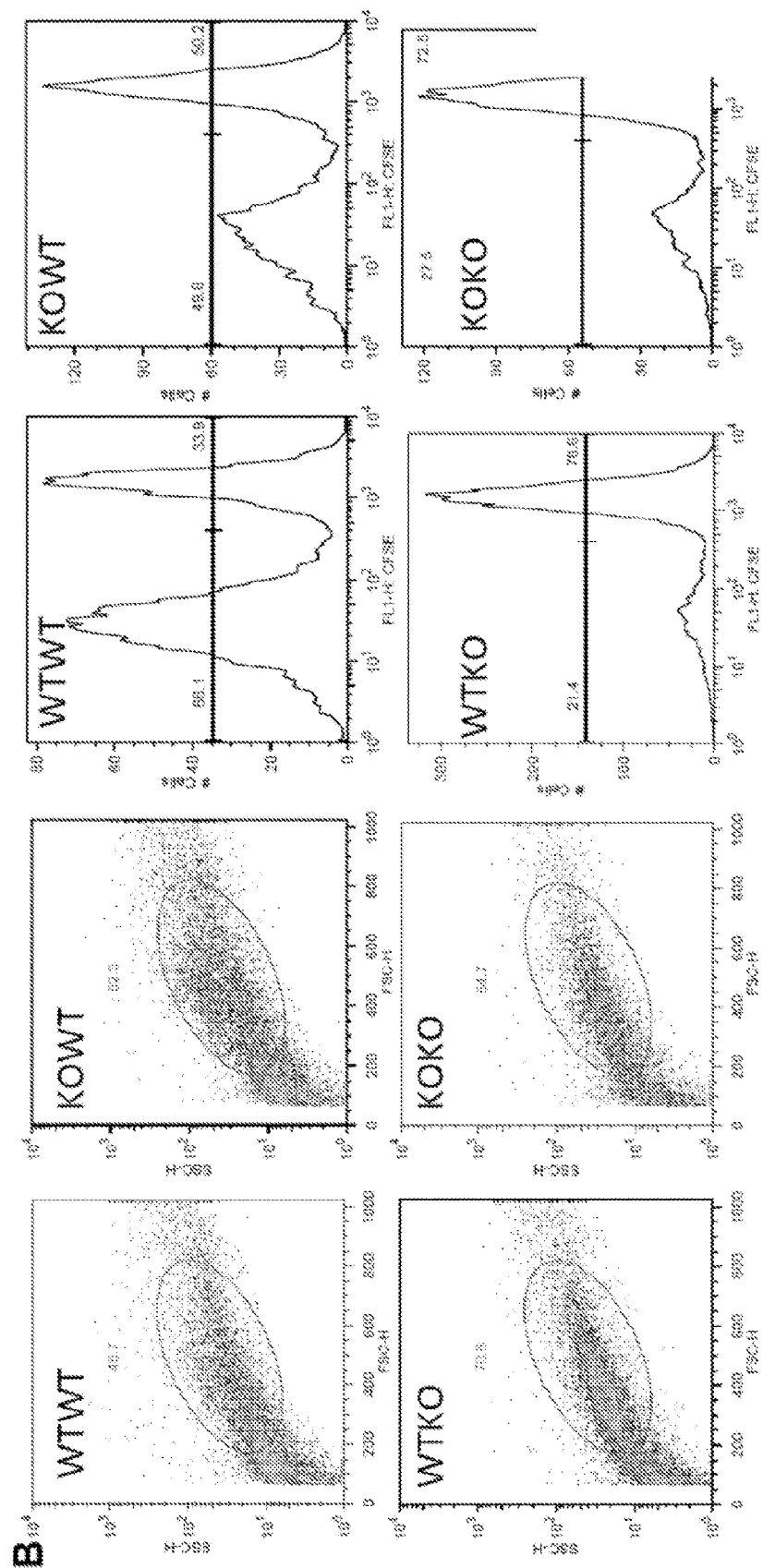
FIG. 3 shows that cultured mast cells demonstrate different reactivity. (A) Bone marrow derived mast cells demonstrate 80-90% positivity for c-kit expression after 4-6 weeks in culture as well as high forward and side scatter profiles by flow cytometry. (B) Co-culture of bone marrow derived mast cells show loss of forward and side scatter profile upon stimulation (left panels) as well as stimulation of proliferation (right panels) demonstrated by loss of CFSE dye. Interestingly, WT and KO mast cells preserved more of their original cell morphology and displayed less proliferation when stimulated by CD13-null dermal fibroblasts. In addition, CD13-null mast cells also maintained more of their original cell morphology and proliferated less than WT mast cells when stimulated with WT dermal fibroblasts.
Figure 8:
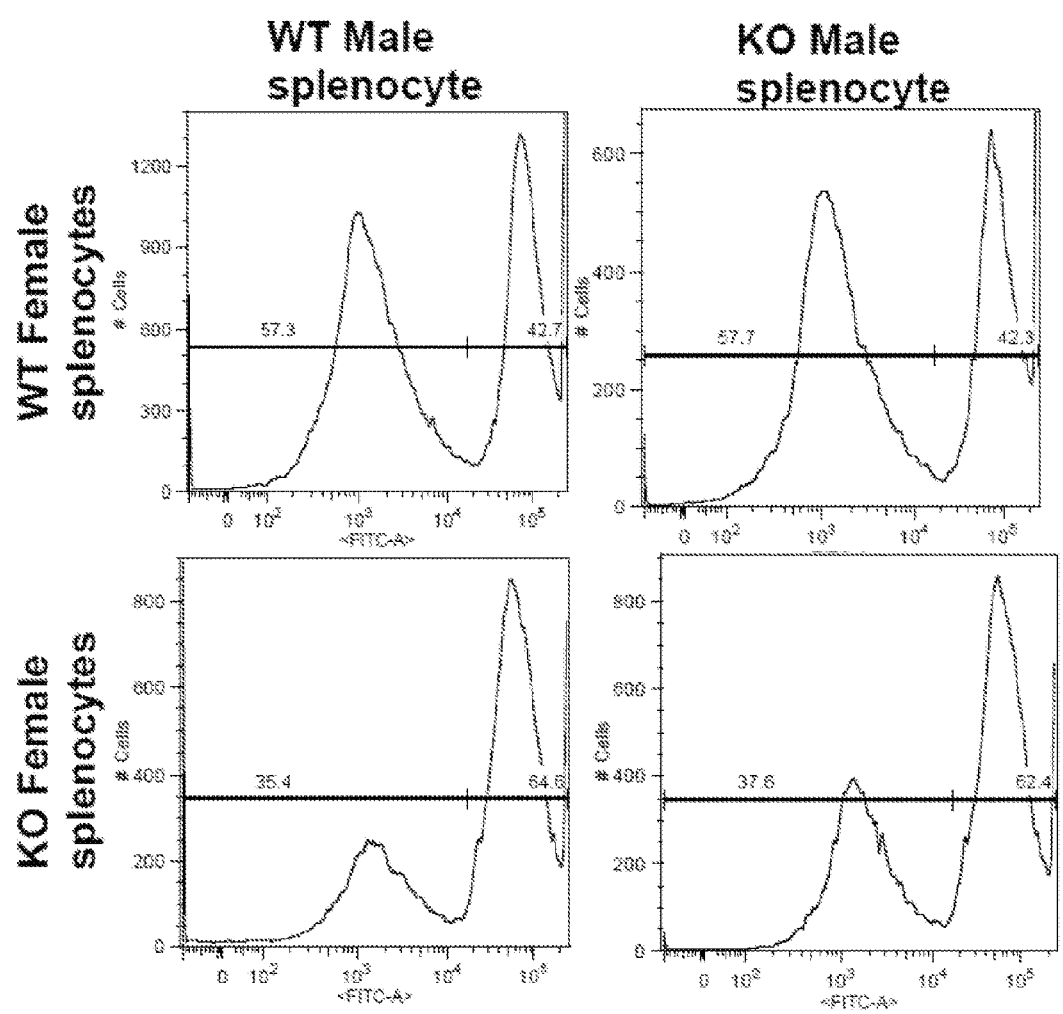
FIG. 8 shows that mixed lymphocyte reactions with WT and CD13-null MiHC mismatched splenocytes show that CD13-null splenocytes demonstrated reduced proliferation upon stimulation compared to WT spienocytes.

Absence of CD13 on Mast Cells Corresponds to Diminished Mast Cell Activation and Degranulation In Vitro To confirm the in vivo observations of effects of CD13 on mast cell activity, primary mast cells were derived from bone marrow of WT and CD13-null mice according to previously published protocols (Kalesnikoff and Jalli 2011). After 4-6 weeks of culture, cultures consisted of 80-90% ckit+FcεR1α+ mast cells with a high degree of forward and side scatter, indicating these cells are large and complex (FIG. 3A). To test the response of mast cells to MiHC determinants, isolated WT or CD13-null mast cells were co-cultured with gender-mismatched dermal fibroblasts and changes were assessed by flow cytometry. The forward and side scatter profiles of both WT and CD13-null mast cells were decreased indicating loss of granularity and size, presumably the result of degranulation; however, the changes in CD13-null mast cell size and granularity were significantly less upon stimulation with either WT or CD13-null dermal fibroblasts than WT mast cells (FIG. 3B). This is in accord with results from mixed lymphocyte reactions between gender mismatched splenocytes where the response of CD13-null splenocytes was considerably weaker (FIG. 8). However, MiHC mismatched CD13-null stimulators invoked more robust responses from WT splenocytes than WT mast cells, suggesting a lack of allorecognition.

Additionally, the supernatant collected from CD13-null mast cells cultured with dermal fibroblasts contained higher levels of IL-4. To determine if CD13-null mast cells could be exerting their anti-inflammatory role at least in part by skewing macrophage differentiation towards the reparative M2 phenotype at the expense of a pro-inflammatory M1 phenotype, WT and CD13-null mast cells are co-cultured with WT and CD13-null immature macrophages for 1-3 days before determining relative numbers of M1 and M2 macrophages by flow cytometry. As a whole, these data show that CD13-null mast cell degranulation and pro-inflammatory responses are impaired while a more anti-inflammatory or immunosuppressive microenvironment is enhanced, thus promoting transplant survival.

Example 6

Transient Blockade of CD13 Prolongs Graft Survival

Figure 4:
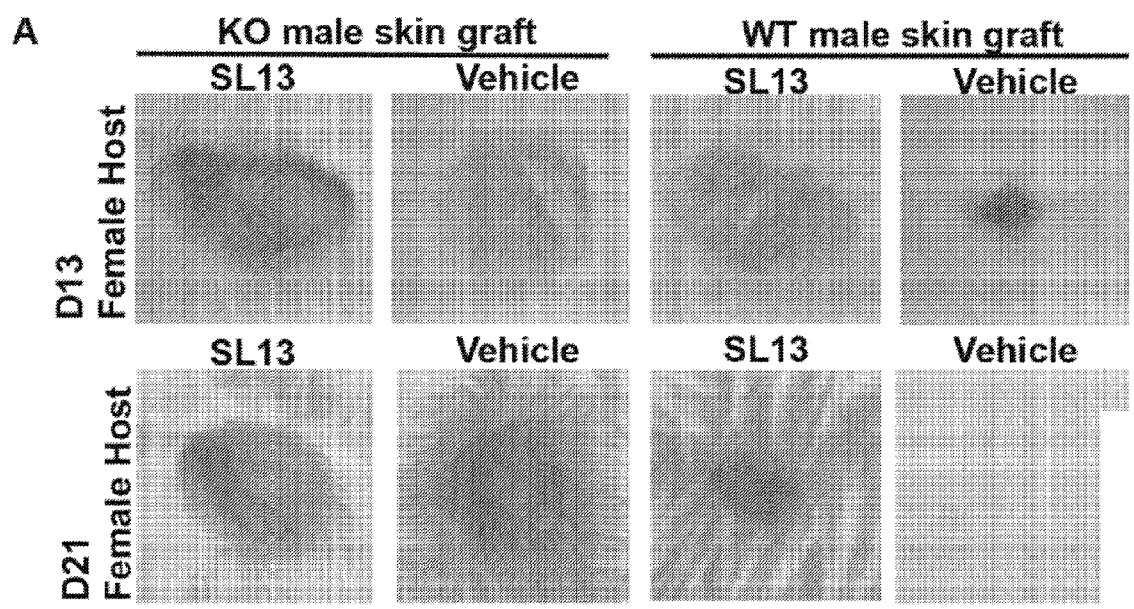
FIG. 4 shows SL13 treatment is sufficient to prolong WT graft survival. (A) WT skin grafts show prolonged survival in WT gender mismatched recipients treated for two weeks with SL13. Vehicle treated controls demonstrated signs of rejection as early as day 13 post-transplant while SL13 treated recipients maintained functional grafts past 3 weeks even after discontinuation of SL13 at time of surgery
Figure 9:
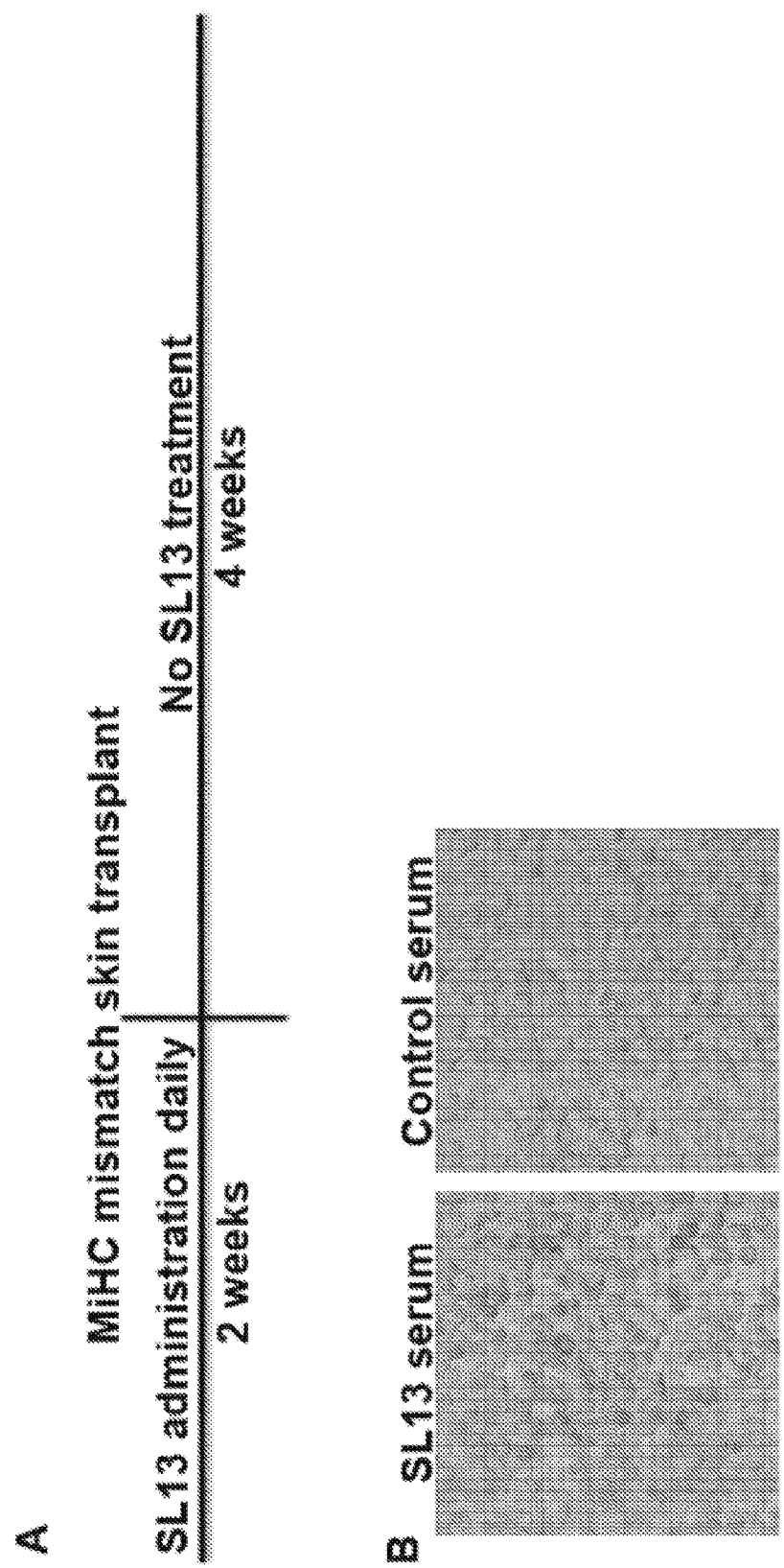
FIG. 9 shows (A) a SL13 treatment Scheme. (B) Check for SL13 antibody in serum of treated and control mice

To confirm the effects on transplant acceptance were due to CD13, a CD13 blocking antibody. SL13, was used in transient treatment studies (FIG. 9A). Following two weeks of intraperitoneal SL13-mAb administration, SL13 was detectable in the serum of treated mice, but not in the serum of mice treated with vehicle alone or isotype control (FIG. 9B). All of the mice tolerated the treatment and after two weeks there were no significant pathological changes in any major organ indicating that SL13 can be used safely in vivo. After the two week treatment period, SL13 treatment was halted and WT female recipients of both groups received gender-mismatched skin grafts from WT and CD13-null male donors. Similar to studies in the global CD13-null animals, CD13-null grafts universally survived until time of harvest in both groups (FIG. 4A left panels; KO male skin graft). Importantly, rejection of WT male skin was delayed by 3 weeks in treated WT recipients, well after WT skin grafts had been rejected by the untreated mice (FIG. 4A right panels; WT male skin graft). Reversal of graft acceptance following the withdrawal of SL13 treatment indicated that CD13 blockade using a monoclonal antibody prolongs graft survival. SL13 treatment for 1 week prior to skin transplant can prolong graft survival when SL13 is routinely given. Once SL13 treatment is discontinued. WT skin grafts show signs of failing. Toluidine blue staining of WT skin that survives in SL13 treated mice indicates an increase in mast cell staining as compared to that seen in CD13-null grafts, suggesting that a similar mechanism of locally induced immune acceptance.

Example 7

Figure 5:
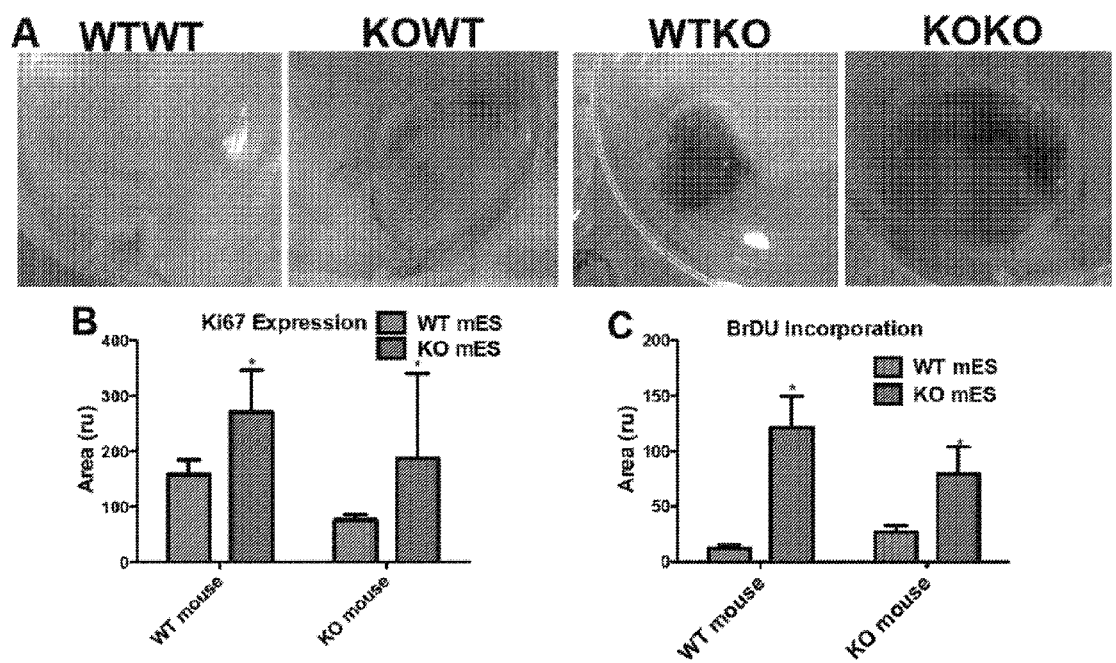
FIG. 5 shows that mES transplantation recapitulates skin graft studies. (A) Gross images of teratomas generated in immune-competent hosts at four weeks shows clear growth advantage cy CD13-null mES as well as apparent growth advantage in CD13-null hosts. (B-C) Proliferation is enhanced in CD13-null teratomas as seen in quantification of Ki67 expression (B) as well as BrDU incorporation (C). (D) This growth advantage is not seen in immune-compromised nude mice. (E) There is less CD3+ T cell infiltration in CD13-null teratomas, especially in those teratomas generated in CD13-null hosts. (F) WT teratomas also demonstrate higher numbers (15% in WT versus 3.29% in CD13 KO) of CD11b+CD11c+ dendritic cells and (G) F4/80+ macrophages by flow cytometry. (H) Toluidine blue staining and quantification of mast cells within teratomas indicate higher levels in CD13-null teratomas.
Figure 5:
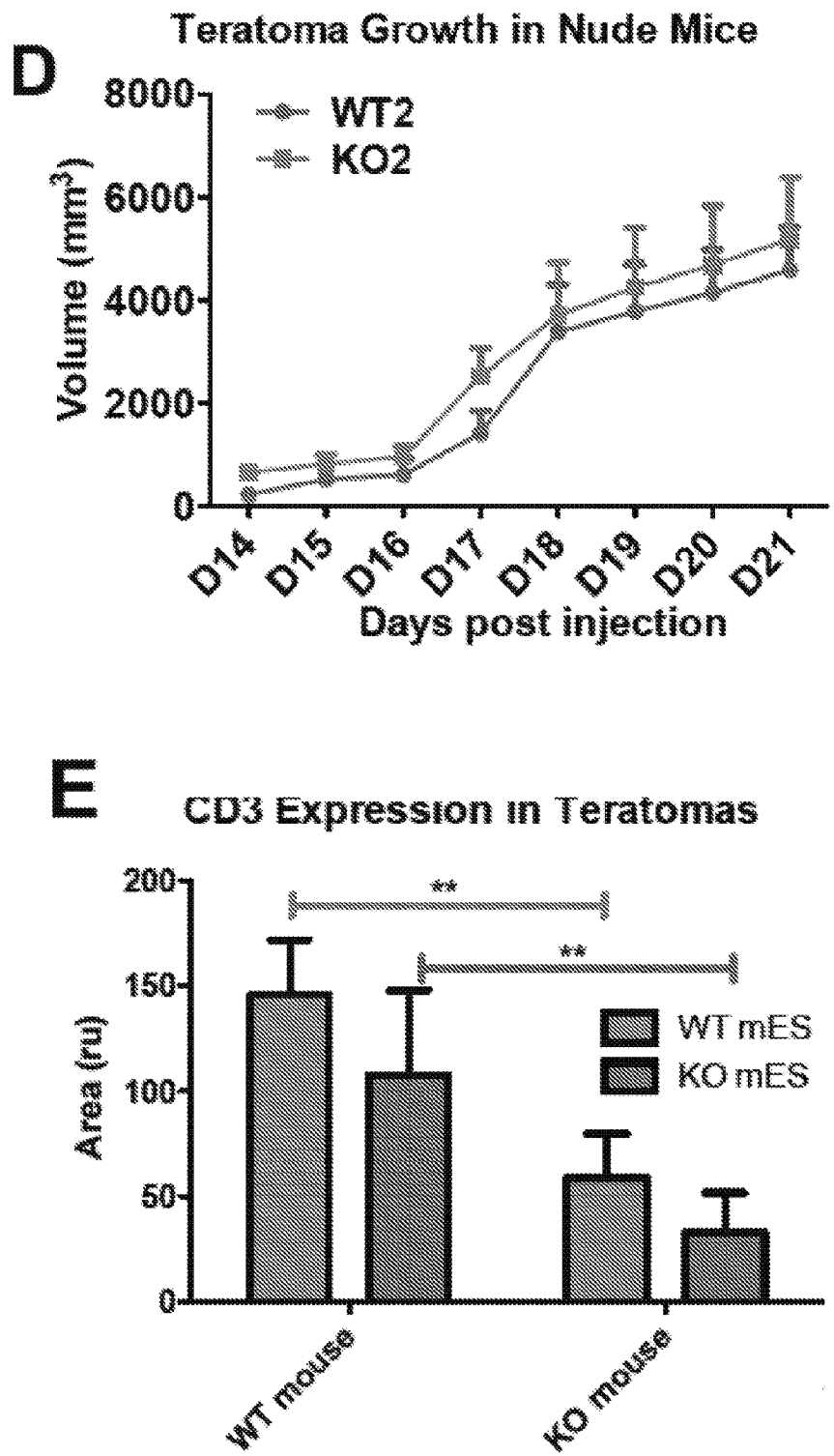
Figure 10:
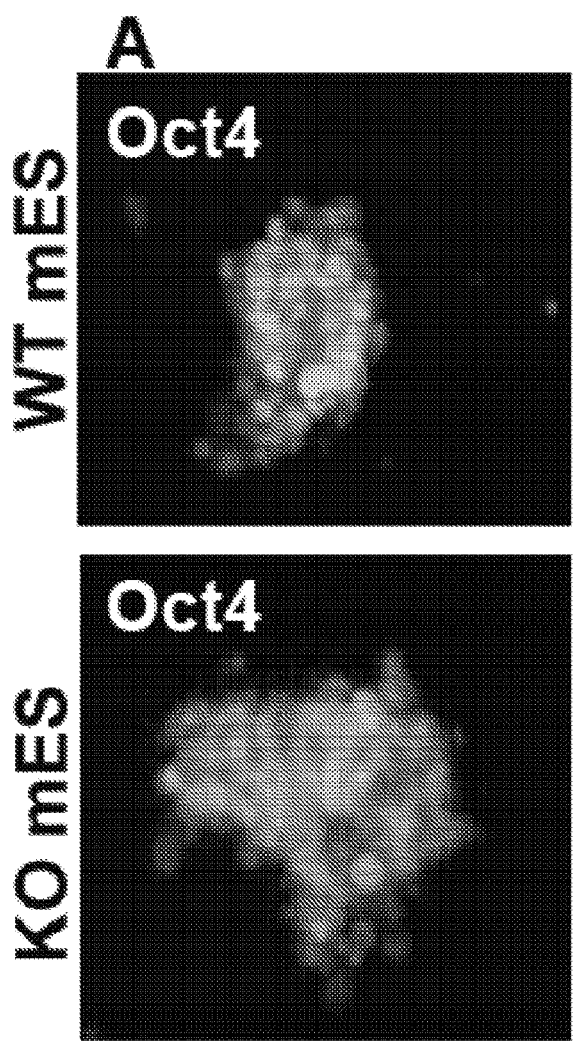
FIG. 10 shows CD13-null mES cell characterization. (A) CD13-null mESCs express the pluripotency marker Oct4. (B) WT mES generate teratomas containing cell types of all three germ layers. (C) CD13-null teratomas also display cell types of all three germ layers. (D) None of the teratomas display any significant apoptosis. (E) CD13-null teratomas contain more CD31 and aSMA positive staining cells, indicating higher levels of vascularity.
Figure 10:
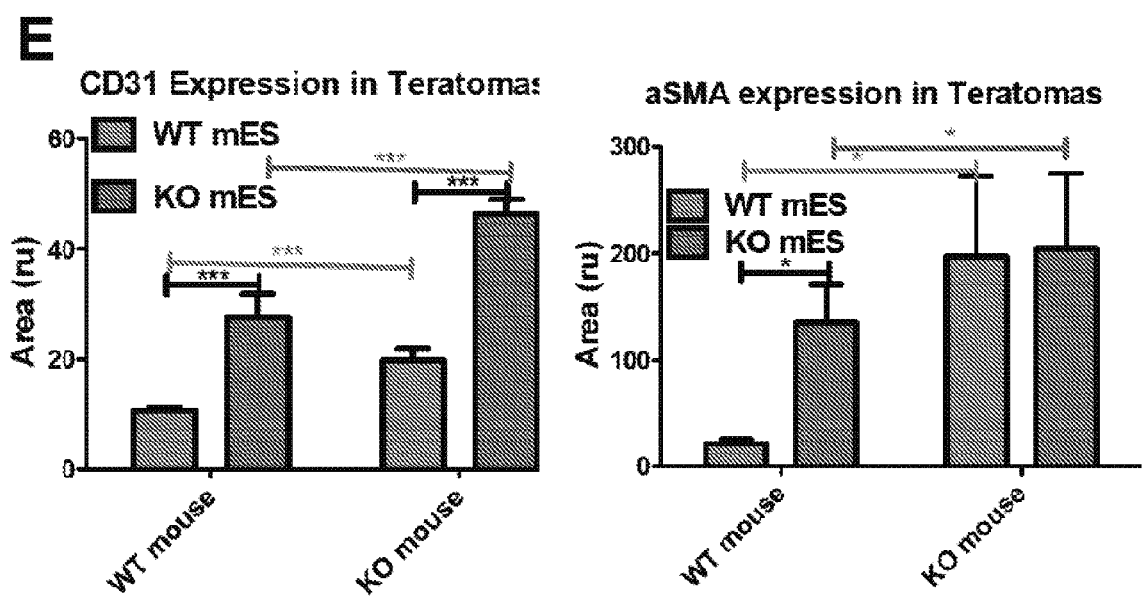

Tissues Derived from mESC Lacking CD13 are Accepted by Immune-competent Mice Pluripotent stem cell derived therapies are the ultimate goal of regenerative medicine; however, their utility in the clinic is hampered by the same immunologic reactions that limit current transplantation therapies (Tang and Drukker 2011). To determine if CD13 blockade could be applied in a stem cell-derived therapeutic setting, mouse embryonic stem cells (mES) were generated from WT and CD13-null mice. These cells displayed characteristic mES cell morphology and expressed traditional pluripotency markers Oct4 and Nanog (FIG. 10A). Both WT and CD13-null mESCs proliferated at similar rates in vitro and generated all three germ layers when differentiated in teratoma assays (FIGS. 10B and 10C). Interestingly, CD13-null mES generated substantially larger teratomas than did WT mES even though starting cell numbers, host mice and duration of growth are matched (FIG. 5A). These CD13-null teratomas also proliferated at higher levels as indicated by increased Ki67 staining and BrDU incorporation (FIGS. 5B and 5C), but did not display any significant apoptosis by Tunel staining (FIG. 10D, arrows indicate apoptotic cells). Furthermore, CD13-null teratomas are also more vascularized as detected by endothelial CD31 and pericyte aSMA staining (FIG. 10E).

Overall, similar to the observations with CD13-null skin grafts these data indicate that CD13-null mES possess a survival advantage over WT mES. To ascertain the potential immunological processes underlying this apparent growth advantage, WT and CD13-null mES were injected subcutaneously into immunocompromised mice lacking T, B and NK cells. Both WT and CD13-null mES generated teratomas of equal size and at similar rates (FIG. 5D) confirming that the difference in growth was not attributable to inherent differences in the embryonic stem cells themselves, but rather to events occurring at the donor-host interface. Analysis of infiltrating immune cells in teratomas generated in immunocompromised mice shows no significant differences; while numbers of infiltrating CD34+ T cells in immune competent mice are higher in WT in CD13-null teratomas. Furthermore, highly significant differences in numbers of infiltrating T cells were observed teratomas generated in CD13-null hosts (FIG. 5E). This would imply that WT mES are more capable of stimulating an immune reaction against the transplanted cells and that the response of CD13-null mice to immunogenic donor cells is impaired and is in agreement with the immune cell analyses in the skin graft studies discussed above. Additionally, higher levels of dendritic cells and macrophages were detected in WT teratomas (FIG. 5F). Toluidine blue staining of teratoma sections also indicated higher levels of mast cell staining within and around CD13-null teratomas, consistent with reduced mast cell degranulation in the skin graft model (FIG. 5G).

Taken together, these data demonstrate that the CD13 blockade-dependent transplant of cells and tissues is most likely due to the absence CD13-mediated immunological rejection. To test the applicability of CD13-blockade in promoting cell therapy, skin and lung cells were generated from male WT and CD13-null mES and transplanted into WT female recipients.

The invention would significantly increase the success of organ and skin transplant as well as eliminate the time transplant recipients must wait for a suitable donor transplant or graft to become available. Furthermore, this invention can minimize the necessity of systemic immune suppression, thereby significantly improving quality of life in terms of avoiding infection and taking medication with deleterious side effects. The method would provide universal transplants or grafts and obviate the need and cost of creating personalized pluripotent cell lines and differentiated tissues that would only be applicable to one or a few patients.

Furthermore, the invention could potentially be used by transplant and reconstructive surgeons for patients who require any type of graft or organ. For example, skin grafts could be used for severely burned patients without the current limitations of time, access to viable skin, or immunogenicity. Neurons or neuronal support cells such as oligodendrocytes could also be produced for transplant into patients suffering from neuromuscular diseases. Cardiac cells could be transplanted into patients who suffered myocardial infarction or congestive heart failure.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

What is claimed is:

1. A method of transplantation comprising:
   (a) pre-treating a subject in need thereof with an effective amount of an inhibitor of alanyl (membrane) aminopeptidase (ANPEP), and
   (b) transplanting a pluripotent cell population into the subject, wherein the pluripotent cell population does not express functional ANPEP.

2. The method of claim 1, wherein the inhibitor is selected from the group consisting of: anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides, and small molecule inhibitors of ANPEP.

3. The method of claim 1, wherein the inhibitor is an anti-ANPEP antibody.

4. The method of claim 1, wherein the cells are syngeneic, allogeneic or xenogeneic to the subject.

5. The method of claim 1, wherein the cells are genetically engineered to express a therapeutic peptide.

6. A method of limiting development of transplant rejection, comprising:
   a) administering to a subject in need of a transplant, and/or b) treating a donor transplant with,
an effective amount of an inhibitor of alanyl (membrane) aminopeptidase (ANPEP) to limit development of transplant rejection in the subject, wherein the subject is receiving a donor transplant or has received a donor transplant and the donor transplant is selected from the group consisting of beta cells, skin cells and skin tissue.

7. The method of claim 6, wherein the subject is receiving a donor transplant or has received a donor transplant and the donor transplant is syngeneic, allogeneic or xenogeneic to the subject.

8. The method of claim 6, wherein the inhibitor is selected from the group consisting of anti-ANPEP antibody, anti-ANPEP aptamer, ANPEP small interfering RNA, ANPEP small internally segmented interfering RNA, ANPEP short hairpin RNA, ANPEP micro RNA, ANPEP antisense oligonucleotides, and small molecule inhibitors of ANPEP.

9. The method of claim 6, wherein the inhibitor comprises an anti-ANPEP antibody.

* * * * *

UNITED STATES PATENT AND TRADEMARK OFFICE
CERTIFICATE OF CORRECTION

PATENT NO. : 9,783,616 B2
APPLICATION NO. : 14/779629
DATED : October 10, 2017
INVENTOR(S) : Linda H. Shapiro et al.

Page 1 of 1

It is certified that error appears in the above-identified patent and that said Letters Patent is hereby corrected as shown below:

In the Specification

Please insert the following paragraph at Column 1, at Line 13:
--Statement of Government Support
This invention was made with government support under Grant No. HL125186, awarded by the NIH. The government has certain rights in the invention.--

Signed and Sealed this
Twenty-fourth Day of July, 2018

Andrei Iancu
*Director of the United States Patent and Trademark Office*

SEQUENCE LISTING

<160> NUMBER OF SEQ ID NOS: 8

<210> SEQ ID NO 1
<211> LENGTH: 967
<212> TYPE: PRT
<213> ORGANISM: Homo sapiens

<400> SEQUENCE: 1

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
                20                  25                  30

Tyr Ser Gln Glu Lys Asn Lys Asn Ala Asn Ser Ser Pro Val Ala Ser
            35                  40                  45

Thr Thr Pro Ser Ala Ser Ala Thr Thr Asn Pro Ala Ser Ala Thr Thr
        50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
            115                 120                 125

Tyr Thr Leu Ser Gln Gly His Arg Val Val Leu Arg Gly Val Gly Gly
        130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
        210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
        290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

```
Phe Asp Pro Leu Ser Ser Ser Ser Asn Lys Glu Arg Val Val Thr
370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
        420                 425                 430

Asp Leu Met Val Leu Asn Asp Val Tyr Arg Val Met Ala Val Asp Ala
            435                 440                 445

Leu Ala Ser Ser His Pro Leu Ser Thr Pro Ala Ser Glu Ile Asn Thr
        450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
                500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
                580                 585                 590

Asp Gly Arg Gln Gln Asp Tyr Trp Leu Ile Asp Val Arg Ala Gln
            595                 600                 605

Asn Asp Leu Phe Ser Thr Ser Gly Asn Glu Trp Val Leu Leu Asn Leu
        610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
                645                 650                 655

Asn Arg Ala Gln Ile Ile Asn Asp Ala Phe Asn Leu Ala Ser Ala His
                660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
        690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
                725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
770                 775                 780
```

```
Asn Asn Pro Ile His Pro Asn Leu Arg Ser Thr Val Tyr Cys Asn Ala
785                 790                 795                 800

Ile Ala Gln Gly Gly Glu Glu Glu Trp Asp Phe Ala Trp Glu Gln Phe
            805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
            835                 840                 845

Leu Asn Pro Asp Leu Ile Arg Lys Gln Asp Ala Thr Ser Thr Ile Ile
            850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
            885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
            915                 920                 925

Gly Phe Gly Ser Gly Thr Arg Ala Leu Glu Gln Ala Leu Glu Lys Thr
            930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 2
<211> LENGTH: 3740
<212> TYPE: DNA
<213> ORGANISM: Homo sapiens

<400> SEQUENCE: 2
gggacggcgg cggcgcagct cggaacccgc cagggtccag ggtccaggtt ccagcgcccg      60
gcggcccagg caccccccga gcccagctcc acacaccgtt cctggatctc ctctccccag     120
gcggagcgtg cccctgccca gtccagtgac cttcgcctgt tggagccctg gttaattttt     180
gcccagtctg cctgttgtgg ggctcctccc ctttggggat ataagcccgg cctggggctg     240
ctccgttctc tgcctggcct gaggctccct gagccgcctc cccaccatca ccatggccaa     300
gggcttctat atttccaagt ccctgggcat cctggggatc ctcctgggcg tggcagccgt     360
gtgcacaatc atcgcactgt cagtggtgta ctcccaggag aagaacaaga cgccaacag      420
ctcccccgtg gcctccacca cccgtccgc ctcagccacc accaaccccg cctcggccac     480
cacccttggac caaagtaaag cgtggaatcg ttaccgcctc cccaacacgc tgaaacccga     540
ttcctaccgg gtgacgctga accgtacct caccccaat gacaggggcc tgtacgtttt     600
taagggctcc agcaccgtcc gtttcacctg caaggaggcc actgacgtca tcatcatcca     660
cagcaagaag ctcaactaca ccctcagcca ggggcacagg gtggtcctgc gtggtgtggg     720
aggctcccag ccccccgaca ttgacaagac tgagctggtg gagcccaccg agtacctggt     780
ggtgcacctc aagggctccc tggtgaagga cagccagtat gagatggaca gcgagttcga     840
gggggagttg gcagatgacc tggcgggctt ctaccgcagc gagtacatgg agggcaatgt     900
cagaaaggtg gtggccacta cacagatgca ggctgcagat gcccggaagt ccttcccatg     960
cttcgatgag ccggccatga aggccgagtt caacatcacg cttatccacc ccaaggacct    1020
gacagccctg tccaacatgc ttcccaaagg tcccagcacc ccacttccag aagaccccaa    1080
```

```
ctggaatgtc actgagttcc acaccacgcc aagatgtcc acgtacttgc tggccttcat      1140
tgtcagtgag ttcgactacg tggagaagca ggcatccaat ggtgtcttga tccggatctg      1200
ggcccggccc agtgccattg cggcgggcca cggcgattat gccctgaacg tgacgggccc      1260
catccttaac ttcttttgctg gtcattatga cacaccctac ccactcccaa aatcagacca     1320
gattggcctg ccagacttca cgccggcgc catggagaac tggggactgg tgacctaccg       1380
ggagaactcc ctgctgttcg accccctgtc ctcctccagc agcaacaagg agcgggtggt      1440
cactgtgatt gctcatgagc tggcccacca gtggttcggg aacctggtga ccatagagtg      1500
gtggaatgac ctgtggctga acgagggctt cgcctcctac gtggagtacc tgggtgctga      1560
ctatgcggag cccacctgga acttgaaaga cctcatggtg ctgaatgatg tgtaccgcgt      1620
gatggcagtg gatgcactgg cctcctccca cccgctgtcc acacccgcct cggagatcaa      1680
cacgccggcc cagatcagtg agctgttttga cgccatctcc tacagcaagg gcgcctcagt    1740
cctcaggatg ctctccagct tcctgtccga ggacgtattc aagcagggcc tggcgtccta     1800
cctccacacc tttgcctacc agaacaccat ctacctgaac ctgtgggacc acctgcagga     1860
ggctgtgaac aaccggtcca tccaactccc caccaccgtg cgggacatca tgaaccgctg     1920
gaccctgcag atgggcttcc cggtcatcac ggtggatacc agcacgggga cccttttccca   1980 ggagcacttc ctccttgacc ccgattccaa tgttacccgc ccctcagaat tcaactacgt     2040
gtggattgtg cccatcacat ccatcagaga tggcagacag cagcaggact actggctgat    2100
agatgtaaga gcccagaacg atctcttcag cacatcaggc aatgagtggg tcctgctgaa    2160
cctcaatgtg acgggctatt accgggtgaa ctacgacgaa gagaactgga ggaagattca    2220
gactcagctg cagagagacc actcggccat ccctgtcatc aatcgggcac agatcattaa    2280
tgacgccttc aacctggcca gtgcccataa ggtccctgtc actctggcgc tgaacaaacac  2340 cctcttcctg attgaagaga acagtacat gccctgggag ccgccctga gcagcctgag     2400 ctacttcaag ctcatgtttg accgctccga ggtctatggc cccatgaaga actacctgaa    2460
gaagcaggtc acaccctct tcattcactt cagaaataat accaacaact ggagggagat     2520
cccagaaaac ctgatggacc agtacagcga ggttaatgcc atcagcaccg cctgctccaa    2580
cggagttcca gagtgtgagg agatggtctc tggccttttc aagcagtgga tggagaaccc    2640
caataataac ccgatccacc ccaacctgcg gtccaccgtc tactgcaacg ctatcgccca    2700
gggcggggag gaggagtggg acttcgcctg ggagcagttc gaaatgccaa cactggtcaa    2760
tgaggctgac aagctccggg cagccctggc ctgcagcaaa gagttgtgga tcctgaacag    2820
gtacctgagc tacaccctga cccggacttt aatccggaag caggacgcca cctctaccat    2880
catcagcatt accaacaacg tcattgggca aggtctggtc tgggactttg tccagagcaa    2940
ctggaagaag ctttttaacg attatggtgg tggctcgttc tccttctcca acctcatcca    3000
ggcagtgaca cgacgattct ccaccgagta tgagctgcag cagctggagc agttcaagaa    3060
ggacaacgag gaaacaggct tcggctcagg caccgggcc ctggagcaag ccctggaaaa    3120
gacgaaagcc aacatcaagt gggtgaagga gaacaaggag gtggtgctcc agtggttcac    3180
agaaaacagc aaatagtccc cagccttga agtcacccgg ccccatgca aggtgccac     3240 atgtgtccat cccagcggct ggtgcagggc ctccattcct ggagcccgag caccagtgt     3300 cctcccctca aggacaaagt ctccagccca cgttctctct gcctgtgagc cagtctagtt   3360
cctgatgacc caggctgcct gagcacctcc cagcccctgc cctcatgcc aacccggccc    3420 taggcctggc atggcacctg tcgcccagtg ccctggggct gatctcaggg aagcccagct   3480
```

```
ccagggccag atgagcagaa gctctcgatg gacaatgaac ggccttgctg ggggccgccc    3540
tgtaccctct ttcacctttc cctaaagacc ctaaatctga ggaatcaaca gggcagcaga    3600
tctgtatatt tttttctaag agaaaatgta aataaaggat ttctagatga aaaaaaaaa     3660 aaaaaaaaaa aaaaaaaaaa aaaaaaaaaa aaaaaaaaaa aaaaaaaaaa aaaaaaaaaa    3720
aaaaaaaaaa aaaaaaaaa                                                  3740

<210> SEQ ID NO 3
<211> LENGTH: 967
<212> TYPE: PRT
<213> ORGANISM: Homo sapiens

<400> SEQUENCE: 3

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
                20                  25                  30

Tyr Ser Gln Glu Lys Asn Lys Asn Ala Asn Ser Ser Pro Val Ala Ser
            35                  40                  45

Thr Thr Pro Ser Ala Ser Ala Thr Thr Asn Pro Ala Ser Ala Thr Thr
        50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320
```

```
Thr Gly Pro Ile Leu Asn Phe Phe Ala Gly His Tyr Asp Thr Pro Tyr
            325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
            355                 360                 365

Phe Asp Pro Leu Ser Ser Ser Ser Asn Lys Glu Arg Val Val Thr
370                 375                 380

Val Ile Ala His Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
            405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
            435                 440                 445

Leu Ala Ser Ser His Pro Leu Ser Thr Pro Ala Ser Glu Ile Asn Thr
450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
            485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
            515                 520                 525

Ser Ile Gln Leu Pro Thr Thr Val Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
            565                 570                 575

Pro Ser Glu Phe Asn Tyr Val Trp Ile Val Pro Ile Thr Ser Ile Arg
            580                 585                 590

Asp Gly Arg Gln Gln Asp Tyr Trp Leu Ile Asp Val Arg Ala Gln
            595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
            645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
            690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
            725                 730                 735
```

```
Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 4
<211> LENGTH: 967
<212> TYPE: PRT
<213> ORGANISM: Homo sapiens

<400> SEQUENCE: 4

Met Ala Lys Gly Phe Tyr Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140
```

```
Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Glu Phe Asn Ile Thr Leu Ile His Pro
225                 230                 235                 240

Lys Asp Leu Thr Ala Leu Ser Asn Met Leu Pro Lys Gly Pro Ser Thr
                245                 250                 255

Pro Leu Pro Glu Asp Pro Asn Trp Asn Val Thr Glu Phe His Thr Thr
            260                 265                 270

Pro Lys Met Ser Thr Tyr Leu Leu Ala Phe Ile Val Ser Glu Phe Asp
        275                 280                 285

Tyr Val Glu Lys Gln Ala Ser Asn Gly Val Leu Ile Arg Ile Trp Ala
    290                 295                 300

Arg Pro Ser Ala Ile Ala Ala Gly His Gly Asp Tyr Ala Leu Asn Val
305                 310                 315                 320

Thr Gly Pro Ile Leu Asn Phe Phe Ala Gly His Tyr Asp Thr Pro Tyr
                325                 330                 335

Pro Leu Pro Lys Ser Asp Gln Ile Gly Leu Pro Asp Phe Asn Ala Gly
            340                 345                 350

Ala Met Glu Asn Trp Gly Leu Val Thr Tyr Arg Glu Asn Ser Leu Leu
        355                 360                 365

Phe Asp Pro Leu Ser Ser Ser Ser Asn Lys Glu Arg Val Val Thr
    370                 375                 380

Val Ile Ala His Glu Leu Ala Ala Gln Trp Phe Gly Asn Leu Val Thr
385                 390                 395                 400

Ile Glu Trp Trp Asn Asp Leu Trp Leu Asn Glu Gly Phe Ala Ser Tyr
                405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
        435                 440                 445

Leu Ala Ser Ser His Pro Leu Ser Thr Pro Ala Ser Glu Ile Asn Thr
    450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
                485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
        515                 520                 525

Ser Ile Gln Leu Pro Thr Thr Val Arg Asp Ile Met Asn Arg Trp Thr
    530                 535                 540

Leu Gln Met Gly Phe Pro Val Ile Thr Val Asp Thr Ser Thr Gly Thr
545                 550                 555                 560
```

```
Leu Ser Gln Glu His Phe Leu Leu Asp Pro Asp Ser Asn Val Thr Arg
                565                 570                 575

Pro Ser Glu Phe Asn Tyr Val Trp Ile Val Pro Ile Thr Ser Ile Arg
            580                 585                 590

Asp Gly Arg Gln Gln Asp Tyr Trp Leu Ile Asp Val Arg Ala Gln
        595                 600                 605

Asn Asp Leu Phe Ser Thr Ser Gly Asn Glu Trp Val Leu Leu Asn Leu
        610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
            645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
        675                 680                 685

Glu Arg Gln Tyr Met Pro Trp Glu Ala Ala Leu Ser Ser Leu Ser Tyr
    690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
            725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
        755                 760                 765

Glu Glu Met Val Ser Gly Leu Phe Lys Gln Trp Met Glu Asn Pro Asn
    770                 775                 780

Asn Asn Pro Ile His Pro Asn Leu Arg Ser Thr Val Tyr Cys Asn Ala
785                 790                 795                 800

Ile Ala Gln Gly Gly Glu Glu Trp Asp Phe Ala Trp Glu Gln Phe
            805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
            885                 890                 895

Ser Phe Ser Asn Leu Ile Gln Ala Val Thr Arg Arg Phe Ser Thr Glu
        900                 905                 910

Tyr Glu Leu Gln Gln Leu Glu Gln Phe Lys Lys Asp Asn Glu Glu Thr
    915                 920                 925

Gly Phe Gly Ser Gly Thr Arg Ala Leu Glu Gln Ala Leu Glu Lys Thr
930                 935                 940

Lys Ala Asn Ile Lys Trp Val Lys Glu Asn Lys Glu Val Val Leu Gln
945                 950                 955                 960

Trp Phe Thr Glu Asn Ser Lys
            965
```

-continued

```
<210> SEQ ID NO 5
<211> LENGTH: 967
<212> TYPE: PRT
<213> ORGANISM: Homo sapiens

<400> SEQUENCE: 5
```

| Met | Ala | Lys | Gly | Phe | Tyr | Ile | Ser | Lys | Ser | Leu | Gly | Ile | Leu | Gly | Ile |
|---|---|---|---|---|---|---|---|---|---|---|---|---|---|---|---|
| 1 | | | | 5 | | | | | 10 | | | | | 15 | |

| Leu | Leu | Gly | Val | Ala | Ala | Val | Cys | Thr | Ile | Ile | Ala | Leu | Ser | Val | Val |
|---|---|---|---|---|---|---|---|---|---|---|---|---|---|---|---|
| | | | 20 | | | | | 25 | | | | | 30 | | |

| Tyr | Ser | Gln | Glu | Lys | Asn | Lys | Asn | Ala | Asn | Ser | Ser | Pro | Val | Ala | Ser |
|---|---|---|---|---|---|---|---|---|---|---|---|---|---|---|---|
| | | | 35 | | | | | 40 | | | | | 45 | | |

| Thr | Thr | Pro | Ser | Ala | Ser | Ala | Thr | Thr | Asn | Pro | Ala | Ser | Ala | Thr | Thr |
|---|---|---|---|---|---|---|---|---|---|---|---|---|---|---|---|
| | 50 | | | | | 55 | | | | | 60 | | | | |

| Leu | Asp | Gln | Ser | Lys | Ala | Trp | Asn | Arg | Tyr | Arg | Leu | Pro | Asn | Thr | Leu |
|---|---|---|---|---|---|---|---|---|---|---|---|---|---|---|---|
| 65 | | | | | 70 | | | | | 75 | | | | | 80 |

| Lys | Pro | Asp | Ser | Tyr | Arg | Val | Thr | Leu | Arg | Pro | Tyr | Leu | Thr | Pro | Asn |
|---|---|---|---|---|---|---|---|---|---|---|---|---|---|---|---|
| | | | | 85 | | | | | 90 | | | | | 95 | |

| Asp | Arg | Gly | Leu | Tyr | Val | Phe | Lys | Gly | Ser | Ser | Thr | Val | Arg | Phe | Thr |
|---|---|---|---|---|---|---|---|---|---|---|---|---|---|---|---|
| | | | 100 | | | | | 105 | | | | | 110 | | |

| Cys | Lys | Glu | Ala | Thr | Asp | Val | Ile | Ile | Ile | His | Ser | Lys | Lys | Leu | Asn |
|---|---|---|---|---|---|---|---|---|---|---|---|---|---|---|---|
| | | | 115 | | | | | 120 | | | | | 125 | | |

| Tyr | Thr | Leu | Ser | Gln | Gly | His | Arg | Val | Val | Leu | Arg | Gly | Val | Gly | Gly |
|---|---|---|---|---|---|---|---|---|---|---|---|---|---|---|---|
| | 130 | | | | | 135 | | | | | 140 | | | | |

| Ser | Gln | Pro | Pro | Asp | Ile | Asp | Lys | Thr | Glu | Leu | Val | Glu | Pro | Thr | Glu |
|---|---|---|---|---|---|---|---|---|---|---|---|---|---|---|---|
| 145 | | | | | 150 | | | | | 155 | | | | | 160 |

| Tyr | Leu | Val | Val | His | Leu | Lys | Gly | Ser | Leu | Val | Lys | Asp | Ser | Gln | Tyr |
|---|---|---|---|---|---|---|---|---|---|---|---|---|---|---|---|
| | | | | 165 | | | | | 170 | | | | | 175 | |

| Glu | Met | Asp | Ser | Glu | Phe | Glu | Gly | Glu | Leu | Ala | Asp | Asp | Leu | Ala | Gly |
|---|---|---|---|---|---|---|---|---|---|---|---|---|---|---|---|
| | | | 180 | | | | | 185 | | | | | 190 | | |

| Phe | Tyr | Arg | Ser | Glu | Tyr | Met | Glu | Gly | Asn | Val | Arg | Lys | Val | Val | Ala |
|---|---|---|---|---|---|---|---|---|---|---|---|---|---|---|---|
| | | | 195 | | | | | 200 | | | | | 205 | | |

| Thr | Thr | Gln | Met | Gln | Ala | Ala | Asp | Ala | Arg | Lys | Ser | Phe | Pro | Cys | Phe |
|---|---|---|---|---|---|---|---|---|---|---|---|---|---|---|---|
| | 210 | | | | | 215 | | | | | 220 | | | | |

| Asp | Glu | Pro | Ala | Met | Lys | Ala | Glu | Phe | Asn | Ile | Thr | Leu | Ile | His | Pro |
|---|---|---|---|---|---|---|---|---|---|---|---|---|---|---|---|
| 225 | | | | | 230 | | | | | 235 | | | | | 240 |

| Lys | Asp | Leu | Thr | Ala | Leu | Ser | Asn | Met | Leu | Pro | Lys | Gly | Pro | Ser | Thr |
|---|---|---|---|---|---|---|---|---|---|---|---|---|---|---|---|
| | | | | 245 | | | | | 250 | | | | | 255 | |

| Pro | Leu | Pro | Glu | Asp | Pro | Asn | Trp | Asn | Val | Thr | Glu | Phe | His | Thr | Thr |
|---|---|---|---|---|---|---|---|---|---|---|---|---|---|---|---|
| | | | 260 | | | | | 265 | | | | | 270 | | |

| Pro | Lys | Met | Ser | Thr | Tyr | Leu | Leu | Ala | Phe | Ile | Val | Ser | Glu | Phe | Asp |
|---|---|---|---|---|---|---|---|---|---|---|---|---|---|---|---|
| | | | 275 | | | | | 280 | | | | | 285 | | |

| Tyr | Val | Glu | Lys | Gln | Ala | Ser | Asn | Gly | Val | Leu | Ile | Arg | Ile | Trp | Ala |
|---|---|---|---|---|---|---|---|---|---|---|---|---|---|---|---|
| | 290 | | | | | 295 | | | | | 300 | | | | |

| Arg | Pro | Ser | Ala | Ile | Ala | Ala | Gly | His | Gly | Asp | Tyr | Ala | Leu | Asn | Val |
|---|---|---|---|---|---|---|---|---|---|---|---|---|---|---|---|
| 305 | | | | | 310 | | | | | 315 | | | | | 320 |

| Thr | Gly | Pro | Ile | Leu | Asn | Phe | Phe | Ala | Gly | His | Tyr | Asp | Thr | Pro | Tyr |
|---|---|---|---|---|---|---|---|---|---|---|---|---|---|---|---|
| | | | | 325 | | | | | 330 | | | | | 335 | |

| Pro | Leu | Pro | Lys | Ser | Asp | Gln | Ile | Gly | Leu | Pro | Asp | Phe | Asn | Ala | Gly |
|---|---|---|---|---|---|---|---|---|---|---|---|---|---|---|---|
| | | | 340 | | | | | 345 | | | | | 350 | | |

| Ala | Met | Glu | Asn | Trp | Gly | Leu | Val | Thr | Tyr | Arg | Glu | Asn | Ser | Leu | Leu |
|---|---|---|---|---|---|---|---|---|---|---|---|---|---|---|---|
| | | | 355 | | | | | 360 | | | | | 365 | | |

| Phe | Asp | Pro | Leu | Ser | Ser | Ser | Ser | Asn | Lys | Glu | Arg | Val | Val | Thr |
|---|---|---|---|---|---|---|---|---|---|---|---|---|---|---|
| | 370 | | | | | 375 | | | | | 380 | | | |

```
Val Ile Ala Ala Glu Leu Ala His Gln Trp Phe Gly Asn Leu Val Thr
385                 390                 395                 400

Ile Glu Trp Trp Asn Asp Leu Trp Leu Asn Glu Gly Phe Ala Ser Tyr
            405                 410                 415

Val Glu Tyr Leu Gly Ala Asp Tyr Ala Glu Pro Thr Trp Asn Leu Lys
            420                 425                 430

Asp Leu Met Val Leu Asn Asp Val Tyr Arg Val Met Ala Val Asp Ala
            435                 440                 445

Leu Ala Ser Ser His Pro Leu Ser Thr Pro Ala Ser Glu Ile Asn Thr
450                 455                 460

Pro Ala Gln Ile Ser Glu Leu Phe Asp Ala Ile Ser Tyr Ser Lys Gly
465                 470                 475                 480

Ala Ser Val Leu Arg Met Leu Ser Ser Phe Leu Ser Glu Asp Val Phe
            485                 490                 495

Lys Gln Gly Leu Ala Ser Tyr Leu His Thr Phe Ala Tyr Gln Asn Thr
            500                 505                 510

Ile Tyr Leu Asn Leu Trp Asp His Leu Gln Glu Ala Val Asn Asn Arg
            515                 520                 525

Ser Ile Gln Leu Pro Thr Thr Val Arg Asp Ile Met Asn Arg Trp Thr
530                 535                 540

Leu Gln Met Gly Phe Pro Val Ile Thr Val Asp Thr Ser Thr Gly Thr
545                 550                 555                 560

Leu Ser Gln Glu His Phe Leu Leu Asp Pro Asp Ser Asn Val Thr Arg
            565                 570                 575

Pro Ser Glu Phe Asn Tyr Val Trp Ile Val Pro Ile Thr Ser Ile Arg
            580                 585                 590

Asp Gly Arg Gln Gln Asp Tyr Trp Leu Ile Asp Val Arg Ala Gln
            595                 600                 605

Asn Asp Leu Phe Ser Thr Ser Gly Asn Glu Trp Val Leu Leu Asn Leu
            610                 615                 620

Asn Val Thr Gly Tyr Tyr Arg Val Asn Tyr Asp Glu Glu Asn Trp Arg
625                 630                 635                 640

Lys Ile Gln Thr Gln Leu Gln Arg Asp His Ser Ala Ile Pro Val Ile
            645                 650                 655

Asn Arg Ala Gln Ile Ile Asn Asp Ala Phe Asn Leu Ala Ser Ala His
            660                 665                 670

Lys Val Pro Val Thr Leu Ala Leu Asn Asn Thr Leu Phe Leu Ile Glu
            675                 680                 685

Glu Arg Gln Tyr Met Pro Trp Glu Ala Ala Leu Ser Ser Leu Ser Tyr
            690                 695                 700

Phe Lys Leu Met Phe Asp Arg Ser Glu Val Tyr Gly Pro Met Lys Asn
705                 710                 715                 720

Tyr Leu Lys Lys Gln Val Thr Pro Leu Phe Ile His Phe Arg Asn Asn
            725                 730                 735

Thr Asn Asn Trp Arg Glu Ile Pro Glu Asn Leu Met Asp Gln Tyr Ser
            740                 745                 750

Glu Val Asn Ala Ile Ser Thr Ala Cys Ser Asn Gly Val Pro Glu Cys
            755                 760                 765

Glu Glu Met Val Ser Gly Leu Phe Lys Gln Trp Met Glu Asn Pro Asn
            770                 775                 780

Asn Asn Pro Ile His Pro Asn Leu Arg Ser Thr Val Tyr Cys Asn Ala
785                 790                 795                 800
```

-continued

Ile Ala Gln Gly Gly Glu Glu Trp Asp Phe Ala Trp Glu Gln Phe
                805                 810                 815

Arg Asn Ala Thr Leu Val Asn Glu Ala Asp Lys Leu Arg Ala Ala Leu
            820                 825                 830

Ala Cys Ser Lys Glu Leu Trp Ile Leu Asn Arg Tyr Leu Ser Tyr Thr
        835                 840                 845

Leu Asn Pro Asp Leu Ile Arg Lys Gln Asp Ala Thr Ser Thr Ile Ile
    850                 855                 860

Ser Ile Thr Asn Asn Val Ile Gly Gln Gly Leu Val Trp Asp Phe Val
865                 870                 875                 880

Gln Ser Asn Trp Lys Lys Leu Phe Asn Asp Tyr Gly Gly Gly Ser Phe
                885                 890                 895

Ser Phe Ser Asn Leu Ile Gln Ala Val Thr Arg Arg Phe Ser Thr Glu
            900                 905                 910

Tyr Glu Leu Gln Gln Leu Glu Gln Phe Lys Lys Asp Asn Glu Glu Thr
        915                 920                 925

Gly Phe Gly Ser Gly Thr Arg Ala Leu Glu Gln Ala Leu Glu Lys Thr
    930                 935                 940

Lys Ala Asn Ile Lys Trp Val Lys Glu Asn Lys Glu Val Val Leu Gln
945                 950                 955                 960

Trp Phe Thr Glu Asn Ser Lys
                965

<210> SEQ ID NO 6
<211> LENGTH: 966
<212> TYPE: PRT
<213> ORGANISM: Homo sapiens

<400> SEQUENCE: 6

Met Ala Lys Gly Phe Phe Ile Ser Lys Ser Leu Gly Ile Leu Gly Ile
1               5                   10                  15

Leu Leu Gly Val Ala Ala Val Cys Thr Ile Ile Ala Leu Ser Val Val
            20                  25                  30

Tyr Ser Gln Glu Lys Asn Lys Asn Ala Asn Ser Ser Pro Val Ala Ser
        35                  40                  45

Thr Thr Pro Ser Ala Ser Ala Thr Thr Asn Pro Ala Ser Ala Thr Thr
    50                  55                  60

Leu Asp Gln Ser Lys Ala Trp Asn Arg Tyr Arg Leu Pro Asn Thr Leu
65                  70                  75                  80

Lys Pro Asp Ser Tyr Arg Val Thr Leu Arg Pro Tyr Leu Thr Pro Asn
                85                  90                  95

Asp Arg Gly Leu Tyr Val Phe Lys Gly Ser Ser Thr Val Arg Phe Thr
            100                 105                 110

Cys Lys Glu Ala Thr Asp Val Ile Ile Ile His Ser Lys Lys Leu Asn
        115                 120                 125

Tyr Thr Leu Ser Gln Gly His Arg Val Val Leu Arg Gly Val Gly Gly
    130                 135                 140

Ser Gln Pro Pro Asp Ile Asp Lys Thr Glu Leu Val Glu Pro Thr Glu
145                 150                 155                 160

Tyr Leu Val Val His Leu Lys Gly Ser Leu Val Lys Asp Ser Gln Tyr
                165                 170                 175

Glu Met Asp Ser Glu Phe Glu Gly Glu Leu Ala Asp Asp Leu Ala Gly
            180                 185                 190

Phe Tyr Arg Ser Glu Tyr Met Glu Gly Asn Val Arg Lys Val Val Ala
        195                 200                 205

```
Thr Thr Gln Met Gln Ala Ala Asp Ala Arg Lys Ser Phe Pro Cys Phe
    210                 215                 220
Asp Glu Pro Ala Met Lys Ala Glu Phe Asn Ile Thr Leu Ile His Pro
225                 230                 235                 240
Lys Asp Leu Thr Ala Leu Ser Asn Met Leu Pro Lys Gly Pro Ser Thr
                245                 250                 255
Pro Leu Pro Glu Asp Pro Asn Trp Asn Val Thr Glu Phe His Thr Thr
            260                 265                 270
Pro Lys Met Ser Thr Tyr Leu Leu Ala Phe Ile Val Ser Glu Phe Asp
        275                 280                 285
Tyr Val Glu Lys Gln Ala Ser Asn Gly Val Leu Ile Arg Ile Trp Ala
290                 295                 300
Arg Pro Ser Ala Ile Ala Ala Gly His Gly Asp Tyr Ala Leu Asn Val
305                 310                 315                 320
Thr Gly Pro Ile Leu Asn Phe Phe Ala Gly His Tyr Asp Thr Pro Tyr
                325                 330                 335
Pro Leu Pro Lys Ser Asp Gln Ile Gly Leu Pro Asp Phe Asn Ala Gly
            340                 345                 350
Ala Met Glu Asn Trp Gly Leu Val Thr Tyr Arg Glu Asn Ser Leu Leu
        355                 360                 365
Phe Asp Pro Leu Ser Ser Ser Ser Asn Lys Glu Arg Val Val Thr
370                 375                 380
Val Ile His Glu Leu Ala His Gln Trp Phe Gly Asn Leu Val Thr Ile
385                 390                 395                 400
Glu Trp Trp Asn Asp Leu Trp Leu Asn Glu Gly Phe Ala Ser Tyr Val
                405                 410                 415
Glu Tyr Leu Gly Ala Asp Tyr Ala Glu Pro Thr Trp Asn Leu Lys Asp
            420                 425                 430
Leu Met Val Leu Asn Asp Val Tyr Arg Val Met Ala Val Asp Ala Leu
        435                 440                 445
Ala Ser Ser His Pro Leu Ser Thr Pro Ala Ser Glu Ile Asn Thr Pro
450                 455                 460
Ala Gln Ile Ser Glu Leu Phe Asp Ala Ile Ser Tyr Ser Lys Gly Ala
465                 470                 475                 480
Ser Val Leu Arg Met Leu Ser Ser Phe Leu Ser Glu Asp Val Phe Lys
                485                 490                 495
Gln Gly Leu Ala Ser Tyr Leu His Thr Phe Ala Tyr Gln Asn Thr Ile
            500                 505                 510
Tyr Leu Asn Leu Trp Asp His Leu Gln Glu Ala Val Asn Asn Arg Ser
        515                 520                 525
Ile Gln Leu Pro Thr Thr Val Arg Asp Ile Met Asn Arg Trp Thr Leu
530                 535                 540
Gln Met Gly Phe Pro Val Ile Thr Val Asp Thr Ser Thr Gly Thr Leu
545                 550                 555                 560
Ser Gln Glu His Phe Leu Leu Asp Pro Asp Ser Asn Val Thr Arg Pro
                565                 570                 575
Ser Glu Phe Asn Tyr Val Trp Ile Val Pro Ile Thr Ser Ile Arg Asp
            580                 585                 590
Gly Arg Gln Gln Gln Asp Tyr Trp Leu Ile Asp Val Arg Ala Gln Asn
        595                 600                 605
Asp Leu Phe Ser Thr Ser Gly Asn Glu Trp Val Leu Leu Asn Leu Asn
610                 615                 620
```

```
Val Thr Gly Tyr Tyr Arg Val Asn Tyr Asp Glu Asn Trp Arg Lys
625                 630                 635                 640

Ile Gln Thr Gln Leu Gln Arg Asp His Ser Ala Ile Pro Val Ile Asn
            645                 650                 655

Arg Ala Gln Ile Ile Asn Asp Ala Phe Asn Leu Ala Ser Ala His Lys
        660                 665                 670

Val Pro Val Thr Leu Ala Leu Asn Asn Thr Leu Phe Leu Ile Glu Glu
    675                 680                 685

Arg Gln Tyr Met Pro Trp Glu Ala Ala Leu Ser Ser Leu Ser Tyr Phe
690                 695                 700

Lys Leu Met Phe Asp Arg Ser Glu Val Tyr Gly Pro Met Lys Asn Tyr
705                 710                 715                 720

Leu Lys Lys Gln Val Thr Pro Leu Phe Ile His Phe Arg Asn Asn Thr
                725                 730                 735

Asn Asn Trp Arg Glu Ile Pro Glu Asn Leu Met Asp Gln Tyr Ser Glu
            740                 745                 750

Val Asn Ala Ile Ser Thr Ala Cys Ser Asn Gly Val Pro Glu Cys Glu
        755                 760                 765

Glu Met Val Ser Gly Leu Phe Lys Gln Trp Met Glu Asn Pro Asn Asn
770                 775                 780

Asn Pro Ile His Pro Asn Leu Arg Ser Thr Val Tyr Cys Asn Ala Ile
785                 790                 795                 800

Ala Gln Gly Gly Glu Glu Trp Asp Phe Ala Trp Glu Gln Phe Arg
                805                 810                 815

Asn Ala Thr Leu Val Asn Glu Ala Asp Lys Leu Arg Ala Ala Leu Ala
            820                 825                 830

Cys Ser Lys Glu Leu Trp Ile Leu Asn Arg Tyr Leu Ser Tyr Thr Leu
        835                 840                 845

Asn Pro Asp Leu Ile Arg Lys Gln Asp Ala Thr Ser Thr Ile Ile Ser
850                 855                 860

Ile Thr Asn Asn Val Ile Gly Gln Gly Leu Val Trp Asp Phe Val Gln
865                 870                 875                 880

Ser Asn Trp Lys Lys Leu Phe Asn Asp Tyr Gly Gly Gly Ser Phe Ser
                885                 890                 895

Phe Ser Asn Leu Ile Gln Ala Val Thr Arg Arg Phe Ser Thr Glu Tyr
            900                 905                 910

Glu Leu Gln Gln Leu Glu Gln Phe Lys Lys Asp Asn Glu Glu Thr Gly
        915                 920                 925

Phe Gly Ser Gly Thr Arg Ala Leu Glu Gln Ala Leu Glu Lys Thr Lys
    930                 935                 940

Ala Asn Ile Lys Trp Val Lys Glu Asn Lys Glu Val Val Leu Gln Trp
945                 950                 955                 960

Phe Thr Glu Asn Ser Lys
                965

<210> SEQ ID NO 7
<211> LENGTH: 3439
<212> TYPE: DNA
<213> ORGANISM: Mus musculus

<400> SEQUENCE: 7
ggcagtgggg ctccaccccc tgtgaggata taagctggcc ccggggctgc tgttctttcc      60
tcttggcctg agctattccg agctccctgt ccaccggcat catggccaag gggtctctaca   120 tttccaagac cctgggcatc ttgggcatcc tgttgggtgt ggcagctgtg tgtaccatca   180
```

```
tagctctgtc ggtggtctac gctcaggaga agaataggaa tgcagagaac tctgccacag    240
cccccacgct cccgggcagc acctcagcca ccaccgcaac caccacccct gctgtagatg    300
aaagcaagcc ttggaaccag tatcgcttgc ctaagactct tatacctgac tcctaccggg    360
tgatcctgag accctacctc accccccaaca atcagggcct gtacatcttc caaggcaaca    420
gtactgttcg ctttacctgc aaccagacca cggatgtcat tatcatccac agcaaaaagc    480
tcaactacac cctcaaagga aaccacaggg tggtgttgcg aaccctggac ggcactccgg    540
cacctaacat tgacaaaacg gaactggtag agcgtactga gtacctggtg gtgcacctgc    600
aggggtccct ggtagagggc cgtcagtacg agatggacag ccagttccag ggggaactgg    660
ctgatgacct ggctggcttc taccgcagcg agtacatgga aggagacgtc aagaaagtgg    720
tggctacaac gcagatgcag gctgctgatg ctcggaaatc ctttccatgt tttgatgagc    780
cagccatgaa ggccatgttc aacatcacac tcatctaccc caacaacctc atagctctgt    840
ctaatatgct tcccaaagag tccaagccct atccggaaga cccttcctgc accatgactg    900
agttccactc caccccctaag atgtccacat acctgctggc ctacatcgtg agcgagttca    960
aaaatataag ctccgtctca gccaatggtg tccagattgg aatctgggct cggcccagtg   1020
ccattgatga gggccagggt gattacgcac tgaacgttac aggccccatc ctaaatttct   1080
ttgcccaaca ttataataca tcctaccctc taccaaagtc tgaccagatt gccctgcctg   1140
acttcaacgc tggagccatg gagaactggg gtctggtgac ctaccgtgag agctccctgg   1200
tctttgactc tcagtcctcc tccattagca caaggagcg gtggtcact gtgattgctc   1260 acgagctggc ccatcagtgg tttgcaacc tggtgactgt ggcttggtgg aatgatctgt   1320
ggctgaacga gggctttgcc tcctacgtgg aatatctggg tgctgactat gcagagccta   1380
cctggaatct gaaagacctc atggtactga atgatgtgta ccgtgtgatg gccgtggatg   1440
cccttgcctc ctcccaccca ctgtccagtc ctgctgacga gatcaaaaca ccagaccaga   1500
tcatggagct gtttgacagc atcacctaca gcaagggagc ctcagtcatc aggatgctgt   1560
ccagtttcct gacagaggac ctgtttaaga agggcctttc atcttatctc cacacctacc   1620
agtactcgaa caccgtttat ctggacctgt gggaacacct gcaaaaggcc gtgaaccaac   1680
agacagctgt ccaaccccg gccacggtgc gcactatcat ggaccgctgg attctacaga   1740 tgggcttttcc cgttatcact gtgaacacca atacaggaga aatctcccag aaacacttcc   1800
tcctggattc caagtccaac gttacccgcc cctccgagtt taattacatc tggatcgcgc   1860
ccattccatt tctcaaaagt ggacaggagg atcactactg gctggatgtc gagaaaaacc   1920
agagtgcaaa gttccagaca tcctccaatg aatggatctt actgaacatt aacgtaaccg   1980
gctactacct ggttaactat gatgagaaca actggaagaa gcttcagaat cagctgcaaa   2040
cagacctttc tgttatccct gtcatcaacc gagcacagat tatccacgac tccttcaacc   2100
tggccagtgc taaaatgata cccatcaccc tggcgctgga caaccccctc ttcctggtca   2160
aagaggcgga gtacatgccc tggcaggctg ccctgagcag cctcaactac ttcacactca   2220
tgttcgaccg ctcggaggtc tacggcccca tgaagaggta tctgaagaag caagttacgc   2280
ccctcttctt ctacttccaa aatagaacca acaactgggt caaccgtcct ccaacgctga   2340
tggagcagta caatgaaatt aacgccatca gcaccgcctg ttccagtggt ctcaaagagt   2400 gtagggaccct ggtcgttgag ctctatagtc agtggatgaa aaaccctaat aataacacga   2460 tccacccccaa ccttcggtct actgtctact gcaatgccat tgctttcggt ggcgaagaag   2520
agtggaactt tgcttgggaa cagttccgga atgcaactct ggtgaacgaa gcggacaaac   2580
```

-continued

```
tccggtcagc cttggcctgt agcaaagatg tgtggatttt gaacaggtac ctgagttaca   2640
ctctgaaccc ggactacatc cggaagcagg acaccacctc caccatcatc agcattgcca   2700
gcaacgtggc tgggcaccct ctggtttggg actttgtccg aagcaactgg aagaaactgt   2760
ttgagaatta cggtggagga tctttctcct ttgccaatct catccaggga gtgacccggc   2820
gcttctcctc tgagttcgag ctgcagcagc tggagcagtt taaagcggat aactcagcca   2880
caggctttgg caccggcact cgggctctgg agcaagccct ggagaagacg agagccaaca   2940
tcgactgggt gaaggagaac aaagatgcgg tattcaagtg gttcacagag aacagcagtt   3000
agttcctggt tctgagaacc acttgtccca gtatgacacc tcttactatc tcagcagcct   3060
gtgcagggtc tctgtcctca gagctccaga caccagcatc ctactctcaa ggatgaagtc   3120
tccagcctgt ggagccagcc tagctcctaa ctgtcaggct gacggacacc tcccaggtct   3180
tgcaccctca tgccaactct gccccaggtc caggcctctg gggctgatct cagggaagcc   3240
cagctctgaa gctagattta ctggacaaag ggcagcctgg aaagagactc cctgaatgct   3300
ttactatccc tgccccctac ccccaccct accccccacg agatccagaa ccaaagaatc   3360
aacagggcac aagatctata tatattttta agagaaaatg taaataaaga atttctaaaa   3420
tgaaaaaaaa aaaaaaaaa                                                3439
```

```

<210> SEQ ID NO 8
<211> LENGTH: 966
<212> TYPE: PRT
<213> ORGANISM: Mus musculus

<400> SEQUENCE: 8

Met Ala Lys Gly Phe Tyr Ile Ser Lys Thr Leu Gly Ile Leu Gly Ile
1               5                   10                  15

Leu Leu Gly Val Ala Ala Val Cys Thr Ile Ile Ala Leu Ser Val Val
            20                  25                  30

Tyr Ala Gln Glu Lys Asn Arg Asn Ala Glu Asn Ser Ala Thr Ala Pro
        35                  40                  45

Thr Leu Pro Gly Ser Thr Ser Ala Thr Thr Ala Thr Thr Thr Pro Ala
    50                  55                  60

Val Asp Glu Ser Lys Pro Trp Asn Gln Tyr Arg Leu Pro Lys Thr Leu
65                  70                  75                  80

Ile Pro Asp Ser Tyr Arg Val Ile Leu Arg Pro Tyr Leu Thr Pro Asn
                85                  90                  95

Asn Gln Gly Leu Tyr Ile Phe Gln Gly Asn Ser Thr Val Arg Phe Thr
            100                 105                 110

Cys Asn Gln Thr Thr Asp Val Ile Ile Ile His Ser Lys Lys Leu Asn
        115                 120                 125

Tyr Thr Leu Lys Gly Asn His Arg Val Val Leu Arg Thr Leu Asp Gly
    130                 135                 140

Thr Pro Ala Pro Asn Ile Asp Lys Thr Glu Leu Val Glu Arg Thr Glu
145                 150                 155                 160

Tyr Leu Val Val His Leu Gln Gly Ser Leu Val Glu Gly Arg Gln Tyr
                165                 170                 175

Glu Met Asp Ser Gln Phe Gln Gly Glu Leu Ala Asp Asp Leu Ala Gly
            180                 185                 190

Phe Tyr Arg Ser Glu Tyr Met Glu Gly Asp Val Lys Lys Val Val Ala
        195                 200                 205

Thr Thr Gln Met Gln Ala Ala Asp Ala Arg Lys Ser Phe Pro Cys Phe
    210                 215                 220
```

-continued

```
Asp Glu Pro Ala Met Lys Ala Met Phe Asn Ile Thr Leu Ile Tyr Pro
225                 230                 235                 240

Asn Asn Leu Ile Ala Leu Ser Asn Met Leu Pro Lys Glu Ser Lys Pro
            245                 250                 255

Tyr Pro Glu Asp Pro Ser Cys Thr Met Thr Glu Phe His Ser Thr Pro
        260                 265                 270

Lys Met Ser Thr Tyr Leu Leu Ala Tyr Ile Val Ser Glu Phe Lys Asn
    275                 280                 285

Ile Ser Ser Val Ser Ala Asn Gly Val Gln Ile Gly Ile Trp Ala Arg
290                 295                 300

Pro Ser Ala Ile Asp Glu Gly Gln Gly Asp Tyr Ala Leu Asn Val Thr
305                 310                 315                 320

Gly Pro Ile Leu Asn Phe Phe Ala Gln His Tyr Asn Thr Ser Tyr Pro
            325                 330                 335

Leu Pro Lys Ser Asp Gln Ile Ala Leu Pro Asp Phe Asn Ala Gly Ala
        340                 345                 350

Met Glu Asn Trp Gly Leu Val Thr Tyr Arg Glu Ser Ser Leu Val Phe
    355                 360                 365

Asp Ser Gln Ser Ser Ile Ser Asn Lys Glu Arg Val Val Thr Val
370                 375                 380

Ile Ala His Glu Leu Ala His Gln Trp Phe Gly Asn Leu Val Thr Val
385                 390                 395                 400

Ala Trp Trp Asn Asp Leu Trp Leu Asn Glu Gly Phe Ala Ser Tyr Val
            405                 410                 415

Glu Tyr Leu Gly Ala Asp Tyr Ala Glu Pro Thr Trp Asn Leu Lys Asp
        420                 425                 430

Leu Met Val Leu Asn Asp Val Tyr Arg Val Met Ala Val Asp Ala Leu
    435                 440                 445

Ala Ser His Pro Leu Ser Ser Pro Ala Asp Glu Ile Lys Thr Pro
450                 455                 460

Asp Gln Ile Met Glu Leu Phe Asp Ser Ile Thr Tyr Ser Lys Gly Ala
465                 470                 475                 480

Ser Val Ile Arg Met Leu Ser Ser Phe Leu Thr Glu Asp Leu Phe Lys
            485                 490                 495

Lys Gly Leu Ser Ser Tyr Leu His Thr Tyr Gln Tyr Ser Asn Thr Val
        500                 505                 510

Tyr Leu Asp Leu Trp Glu His Leu Gln Lys Ala Val Asn Gln Gln Thr
    515                 520                 525

Ala Val Gln Pro Pro Ala Thr Val Arg Thr Ile Met Asp Arg Trp Ile
530                 535                 540

Leu Gln Met Gly Phe Pro Val Ile Thr Val Asn Thr Asn Thr Gly Glu
545                 550                 555                 560

Ile Ser Gln Lys His Phe Leu Leu Asp Ser Lys Ser Asn Val Thr Arg
            565                 570                 575

Pro Ser Glu Phe Asn Tyr Ile Trp Ile Ala Pro Ile Pro Phe Leu Lys
        580                 585                 590

Ser Gly Gln Glu Asp His Tyr Trp Leu Asp Val Glu Lys Asn Gln Ser
    595                 600                 605

Ala Lys Phe Gln Thr Ser Ser Asn Glu Trp Ile Leu Leu Asn Ile Asn
610                 615                 620

Val Thr Gly Tyr Tyr Leu Val Asn Tyr Asp Glu Asn Asn Trp Lys Lys
625                 630                 635                 640
```

-continued

```
Leu Gln Asn Gln Leu Gln Thr Asp Leu Ser Val Ile Pro Val Ile Asn
                645                 650                 655

Arg Ala Gln Ile Ile His Asp Ser Phe Asn Leu Ala Ser Ala Lys Met
                660                 665                 670

Ile Pro Ile Thr Leu Ala Leu Asp Asn Thr Leu Phe Leu Val Lys Glu
                675                 680                 685

Ala Glu Tyr Met Pro Trp Gln Ala Ala Leu Ser Ser Leu Asn Tyr Phe
                690                 695                 700

Thr Leu Met Phe Asp Arg Ser Glu Val Tyr Gly Pro Met Lys Arg Tyr
705                 710                 715                 720

Leu Lys Lys Gln Val Thr Pro Leu Phe Phe Tyr Phe Gln Asn Arg Thr
                725                 730                 735

Asn Asn Trp Val Asn Arg Pro Pro Thr Leu Met Glu Gln Tyr Asn Glu
                740                 745                 750

Ile Asn Ala Ile Ser Thr Ala Cys Ser Ser Gly Leu Lys Glu Cys Arg
                755                 760                 765

Asp Leu Val Val Glu Leu Tyr Ser Gln Trp Met Lys Asn Pro Asn Asn
            770                 775                 780

Asn Thr Ile His Pro Asn Leu Arg Ser Thr Val Tyr Cys Asn Ala Ile
785                 790                 795                 800

Ala Phe Gly Gly Glu Glu Trp Asn Phe Ala Trp Glu Gln Phe Arg
                805                 810                 815

Asn Ala Thr Leu Val Asn Glu Ala Asp Lys Leu Arg Ser Ala Leu Ala
                820                 825                 830

Cys Ser Lys Asp Val Trp Ile Leu Asn Arg Tyr Leu Ser Tyr Thr Leu
            835                 840                 845

Asn Pro Asp Tyr Ile Arg Lys Gln Asp Thr Thr Ser Thr Ile Ile Ser
850                 855                 860

Ile Ala Ser Asn Val Ala Gly His Pro Leu Val Trp Asp Phe Val Arg
865                 870                 875                 880

Ser Asn Trp Lys Lys Leu Phe Glu Asn Tyr Gly Gly Gly Ser Phe Ser
                885                 890                 895

Phe Ala Asn Leu Ile Gln Gly Val Thr Arg Arg Phe Ser Ser Glu Phe
                900                 905                 910

Glu Leu Gln Gln Leu Glu Gln Phe Lys Ala Asp Asn Ser Ala Thr Gly
            915                 920                 925

Phe Gly Thr Gly Thr Arg Ala Leu Glu Gln Ala Leu Glu Lys Thr Arg
            930                 935                 940

Ala Asn Ile Asp Trp Val Lys Glu Asn Lys Asp Ala Val Phe Lys Trp
945                 950                 955                 960

Phe Thr Glu Asn Ser Ser
                965
```